(12) United States Patent
Andersen

(10) Patent No.: US 12,194,081 B2
(45) Date of Patent: Jan. 14, 2025

(54) ARGINASE1 POLYPEPTIDES

(71) Applicant: IO BIOTECH APS, Copenhagen N (DK)

(72) Inventor: Mads Hald Andersen, Nærum (DK)

(73) Assignee: IO Biotech APS, Copenhagen (DK)

( * ) Notice: Subject to any disclaimer, the term of this patent is extended or adjusted under 35 U.S.C. 154(b) by 668 days.

(21) Appl. No.: 17/278,838

(22) PCT Filed: Sep. 24, 2019

(86) PCT No.: PCT/EP2019/075731
§ 371 (c)(1),
(2) Date: Mar. 23, 2021

(87) PCT Pub. No.: WO2020/064744
PCT Pub. Date: Apr. 2, 2020

(65) Prior Publication Data
US 2022/0031818 A1  Feb. 3, 2022

(30) Foreign Application Priority Data

Sep. 24, 2018  (GB) .................................... 1815549

(51) Int. Cl.
| A61K 38/50 | (2006.01) |
| A61K 39/00 | (2006.01) |
| A61K 45/06 | (2006.01) |
| A61P 35/00 | (2006.01) |
| C12N 9/78 | (2006.01) |

(52) U.S. Cl.
CPC ...... *A61K 38/50* (2013.01); *A61K 39/001154* (2018.08); *A61K 45/06* (2013.01); *A61P 35/00* (2018.01); *C12N 9/78* (2013.01); *C12Y 305/03001* (2013.01)

(58) Field of Classification Search
None
See application file for complete search history.

(56) References Cited

U.S. PATENT DOCUMENTS

| 5,554,372 A | 9/1996 | Hunter |
| 10,858,642 B2 * | 12/2020 | Andersen ............... A61K 38/00 |
| 2003/0228583 A1 | 12/2003 | Amacher et al. |
| 2013/0245237 A1 | 9/2013 | Rush et al. |

(Continued)

FOREIGN PATENT DOCUMENTS

| EP | 0825260 | 2/1998 |
| WO | WO 2006/050313 | 5/2006 |

(Continued)

OTHER PUBLICATIONS

Ahmad et al., "PD-L1 peptide co-stimulation increases immunogenicity of a dendritic cell-based cancer vaccine." in press ed. 2016.

(Continued)

*Primary Examiner* — David W Berke-Schlessel
(74) *Attorney, Agent, or Firm* — COOLEY LLP

(57) ABSTRACT

The present invention relates to novel polypeptides, which are derived from Arginase 1. The invention also relates to polynucleotides encoding the polypeptides. The invention also relates to compositions comprising the polypeptides and polynucleotides. The invention also concerns uses of the polypeptides, polynucleotides, and compositions.

8 Claims, 12 Drawing Sheets

Specification includes a Sequence Listing.

(56) References Cited

U.S. PATENT DOCUMENTS

| | | |
|---|---|---|
| 2016/0250307 A1 | 9/2016 | Weinschenk et al. |
| 2016/0367648 A1 | 12/2016 | Schabbauer et al. |

FOREIGN PATENT DOCUMENTS

| | | | |
|---|---|---|---|
| WO | WO 2010051533 | 5/2010 | |
| WO | WO 2016/102272 | 6/2016 | |
| WO | WO-2018065563 A1 * | 4/2018 | ............. A61K 38/00 |
| WO | WO2018065563 | 12/2018 | |

OTHER PUBLICATIONS

Andersen et al. (1999) "Phosphorylated Peptides Can Be Transported by TAP Molecules, Presented by Class I MHC Molecules, and Recognized by Phosphopeptide-Specific CTL." J Immunol 163:3812-8.
Bronte & Zanovello, (2005) "Regulation of immune responses by L-arginine metabolism." Nat Rev Immunol 5:641-54.
EP examination report for EP App No. 17786870.0 dated Aug. 10, 2021, 5 pages.
Japanese Office Action for Japanese Patent Application No. 2019-518424 dated Aug. 3, 2021, 5 pages. English Translation.
Jeffery, H. et al. The preparation and characterization of poly(lactide-co-glycolide) microparticles. II. The entrapment of a model protein using a (water-in-oil)-in-water emulsion solvent evaporation technique. Pharm Res. Mar. 1993; 10(3):362-8.
Munder, "Arginase: an emerging key player in the mammalian immune system."British Journal of Pharmacol. vol. 158, No. 3, 2009 pp. 638-651.
Mussai et al. (2013), "Acute myeloid leukemia creates an arginase-dependent immunosuppressive microenvironment." Blood 122:749-58.
NCBI GenBank AEB160141 N414477KR, dated Dec. 23, 2010.
Remington's Pharmaceutical Sciences (Mack Pub. Co., N.J. 1990).
Sambrook et al (1989, Molecular Cloning—a laboratory manual; Cold Spring Harbor Press.
Search Report, Singapore Application No. 11201902766R received Jul. 13, 2020, 3 pages.
Wang, Z. et al. Blocking autophagy enhanced cytotoxicity induced by recombinant human arginase in triple-negative breast cancer cells. Cell Death Dis. Dec. 11, 2014;5(12):e1563.
Ahmad, SM, et al. Harnessing PD-L1-specific cytotoxic T cells for anti-leukemia immunotherapy to defeat mechanisms of immune escape mediated by the PD-1 pathway. Leukemia, 2014; 28(1):236-238.
Andersen,MH. CD4 responses against IDO. Oncoimmunology, 2012; 1(7):1211-1212.
Andersen, MH. Anti-regulatory T cells. Semin Immunopathol. Apr. 2017;39(3):317-326.
Andersen, MH. Immune regulation by self-recognition: novel possibilities for anticancer immunotherapy. J. Natl. Cancer Inst. 2015;107:154.
Andersen, MH. The balance players of the adaptive immune system. Cancer Res. 2018, 78(6):1379-1382.
Cassetta, L. et al., Targeting macrophages: therapeutic approaches in cancer. Nat. Rev. Drug Discov. 2018; 17, 887-904.
De Boniface, J, et al., Expression patterns of the immunomodulatory enzyme arginase 1 in blood, lymph nodes and tumor tissue of early-stage breast cancer patients. Oncoimmunology, 2012; 1(8):1305-1312.
Gajewski, TF, et al., Innate and adaptive immune cells in the tumor microenvironment. Nat Immunol 2013, 14(10):1014-1022.
Geiger, R et al. 1-Arginine modulates T cell metabolism and enhances survival and anti-tumor activity. Cell, 2016; 167(3):829-842.
Jørgensen, MA et al. Spontaneous T-cell responses against Arginase-1 in the chronic myeloproliferative neoplasms relative to disease stage and type of driver mutation. Oncoimmunology. Jul. 23, 2018;7(9):e1468957.
Keilholz, U, et al., Immunologic monitoring of cancer vaccine therapy: results of a workshop sponsored by the Society for Biological Therapy. J. Immunother. 2002;25:97-138.
Lang, S et al., Clinical relevance and suppressive capacity of human MDSC subsets. Clin Cancer Res, 2018; 24(19):4834-4844.
Martinenaite, E et al. CCL22-specific T Cells: modulating the immunosuppressive tumor microenvironment. Oncoimmunology, 2016; 5(11):e1238541.
Martinenaite E, et al. Frequent adaptive immune responses against arginase-1. Oncoimmunology. 2018;7(3):1-9.
Martinenaite et al., "Arginase-1-based vaccination against the tumor microenvironment: the identification of an optimal T-cell epitope", Cancer Immunology, Immunotherapy, Nih Author Manuscript, vol. 68, pp. 1901-1907 (2019).
Martinenaite et al., Peripheral memory T cells specific for Arginase-1, Cell Mol Immunol. Aug. 2019; 16(8): 718-719.
Moodie, Z, et al., Response determination criteria for ELISPOT: toward a standard that can be applied across laboratories. Methods Mol Biol. 2012; 792:185-196.
Munder, Th1/Th2-Regulated Expression of Arginase Isoforms in Murine Macrophages and Dendritic Cells, J Immunol 1999; 163(7):3771-3777.
Munir, S, et al., The immune checkpoint regulator PD-L1 is a specific target for naturally occurring CD4(+) T cells. Oncoimmunology, 2013; 2(4):e23991.
Munir, S, et al., Cutaneous T cell lymphoma cells are targets for immune checkpoint ligand PD-L1-specific, cytotoxic T cells. Leukemia, 2013; 27(11):2251-2253.
Munir, S, et al. HLA-restricted cytotoxic T cells that are specific for the immune checkpoint ligand PD-L1 occur with high frequency in cancer patients. Cancer Res. 2013;73(6):1674-1776.
Nair, S, et al., Vaccination against the forkhead family transcription factor Foxp3 enhances tumor immunity. Cancer Res, 2007; 67(1):371-380.
Namdar, A et al., Prophylactic DNA vaccine targeting Foxp3 + regulatory T cells depletes myeloid-derived suppressor cells and improves anti-melanoma immune responses in a murine model. Cancer Immunol Immunother, 2018; 67(3):367-379.
Rodriguez, PC et al Arginase I—producing myeloid-derived suppressor cells in renal cell carcinoma are a subpopulation of activated granulocytes. Cancer Res, 2009;69(4):1553-1561.
Rodriguez, PC, et al., L-arginine availability regulates T-lymphocyte cell-cycle progression. Blood, 2007; 109(4):1568-1574.
Rotondo, R et al. IL-8 induces exocytosis of arginase 1 by neutrophil polymorphonuclears in nonsmall cell lung cancer. Int J Cancer, 2009; 125:887-893.
Singhal, S, et al., Human tumor-associated monocytes/macrophages and their regulation of T cell responses in early-stage lung cancer. Sci. Transl. Med. 2019;11:11-479.
Sorensen, RB, et al., Indoleamine 2,3-dioxygenase specific, cytotoxic T cells as immune regulators. Blood, 2011; 117(7):2200-2210.
Vanpouille-Box, C, et al., Dual transforming growth factor-beta and programmed death-1 blockade: a strategy for immune-excluded tumors? Trends Immunol. 2018;39:435-437.
Yu, W, et al. Clonal deletion prunes but does not eliminate self-specific alphabeta CD8(+) T lymphocytes. Immunity. 2015;19;42:929-941.
Zea, AH et al., L-Arginine modulates CD3 expression and T cell function in activated human T lymphocytes. Cell Immunol, 2004; 232(1-2):21-31.
Kim and Seong, "Peptide Amidation: Production of Peptide Hormones in vivo and in vitro," Biotechnol. Bioprocess Eng. 2001, 6: 244-251.

* cited by examiner

SEQUENCE LISTING

<160> NUMBER OF SEQ ID NOS: 13

<210> SEQ ID NO 1
<211> LENGTH: 38
<212> TYPE: PRT
<213> ORGANISM: Artificial Sequence
<220> FEATURE:
<223> OTHER INFORMATION: Peptide fragment of human Arginase 1 (ArgLong2)

<400> SEQUENCE: 1

Ile Ser Ala Lys Asp Ile Val Tyr Ile Gly Leu Arg Asp Val Asp Pro
1               5                   10                  15

Gly Glu His Tyr Ile Leu Lys Thr Leu Gly Ile Lys Tyr Phe Ser Met
            20                  25                  30

Thr Glu Val Asp Arg Leu
        35

<210> SEQ ID NO 2
<211> LENGTH: 38
<212> TYPE: PRT
<213> ORGANISM: Artificial Sequence
<220> FEATURE:
<223> OTHER INFORMATION: Peptide fragment of murine Arginase 1
      (mArgLong2)

<400> SEQUENCE: 2

Ile Ser Ala Lys Asp Ile Val Tyr Ile Gly Leu Arg Asp Val Asp Pro
1               5                   10                  15

Gly Glu His Tyr Ile Ile Lys Thr Leu Gly Ile Lys Tyr Phe Ser Met
            20                  25                  30

Thr Glu Val Asp Lys Leu
        35

<210> SEQ ID NO 3
<211> LENGTH: 32
<212> TYPE: PRT
<213> ORGANISM: Artificial Sequence
<220> FEATURE:
<223> OTHER INFORMATION: Peptide fragment of human Arginase 1 (ArgLong3)

<400> SEQUENCE: 3

Ile Ser Ala Lys Asp Ile Val Tyr Ile Gly Leu Arg Asp Val Asp Pro
1               5                   10                  15

Gly Glu His Tyr Ile Leu Lys Thr Leu Gly Ile Lys Tyr Phe Ser Met
            20                  25                  30

<210> SEQ ID NO 4
<211> LENGTH: 32
<212> TYPE: PRT
<213> ORGANISM: Artificial Sequence

```
<220> FEATURE:
<223> OTHER INFORMATION: Peptide fragment of murine Arginase 1
      (mArgLong3)

<400> SEQUENCE: 4

Ile Ser Ala Lys Asp Ile Val Tyr Ile Gly Leu Arg Asp Val Asp Pro
1               5                   10                  15

Gly Glu His Tyr Ile Ile Lys Thr Leu Gly Ile Lys Tyr Phe Ser Met
            20                  25                  30

<210> SEQ ID NO 5
<211> LENGTH: 42
<212> TYPE: PRT
<213> ORGANISM: Artificial Sequence
<220> FEATURE:
<223> OTHER INFORMATION: Peptide fragment of human Arginase 1 (ArgLong)

<400> SEQUENCE: 5

Ile Ser Ala Lys Asp Ile Val Tyr Ile Gly Leu Arg Asp Val Asp Pro
1               5                   10                  15

Gly Glu His Tyr Ile Leu Lys Thr Leu Gly Ile Lys Tyr Phe Ser Met
            20                  25                  30

Thr Glu Val Asp Arg Leu Gly Ile Gly Lys
        35                  40

<210> SEQ ID NO 6
<211> LENGTH: 42
<212> TYPE: PRT
<213> ORGANISM: Artificial Sequence
<220> FEATURE:
<223> OTHER INFORMATION: Peptide fragment of murine Arginase 1
      (mArgLong)

<400> SEQUENCE: 6

Ile Ser Ala Lys Asp Ile Val Tyr Ile Gly Leu Arg Asp Val Asp Pro
1               5                   10                  15

Gly Glu His Tyr Ile Ile Lys Thr Leu Gly Ile Lys Tyr Phe Ser Met
            20                  25                  30

Thr Glu Val Asp Lys Leu Gly Ile Gly Lys
        35                  40

<210> SEQ ID NO 7
<211> LENGTH: 20
<212> TYPE: PRT
<213> ORGANISM: Artificial Sequence
<220> FEATURE:
<223> OTHER INFORMATION: Peptide fragment of human Arginase 1 (Arg1-18)

<400> SEQUENCE: 7

Ala Lys Asp Ile Val Tyr Ile Gly Leu Arg Asp Val Asp Pro Gly Glu
1               5                   10                  15

His Tyr Ile Leu
            20

<210> SEQ ID NO 8
<211> LENGTH: 20
<212> TYPE: PRT
<213> ORGANISM: Artificial Sequence
<220> FEATURE:
<223> OTHER INFORMATION: Peptide fragment of human Arginase 1 (Arg1-19)

<400> SEQUENCE: 8

Asp Val Asp Pro Gly Glu His Tyr Ile Leu Lys Thr Leu Gly Ile Lys
1               5                   10                  15
```

Tyr Phe Ser Met
            20

<210> SEQ ID NO 9
<211> LENGTH: 20
<212> TYPE: PRT
<213> ORGANISM: Artificial Sequence
<220> FEATURE:
<223> OTHER INFORMATION: Peptide fragment of human Arginase 1 (Arg1-20)

<400> SEQUENCE: 9

Lys Thr Leu Gly Ile Lys Tyr Phe Ser Met Thr Glu Val Asp Arg Leu
1               5                   10                  15

Gly Ile Gly Lys
            20

<210> SEQ ID NO 10
<211> LENGTH: 322
<212> TYPE: PRT
<213> ORGANISM: Homo sapiens

<400> SEQUENCE: 10

Met Ser Ala Lys Ser Arg Thr Ile Gly Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Cys Asp Val Lys
        35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

```
Leu Asp Ile Met Glu Val Asn Pro Ser Leu Gly Lys Thr Pro Glu Glu
            275                 280                 285

Val Thr Arg Thr Val Asn Thr Ala Val Ala Ile Thr Leu Ala Cys Phe
        290                 295                 300

Gly Leu Ala Arg Glu Gly Asn His Lys Pro Ile Asp Tyr Leu Asn Pro
305                 310                 315                 320

Pro Lys

<210> SEQ ID NO 11
<211> LENGTH: 323
<212> TYPE: PRT
<213> ORGANISM: Mus musculus

<400> SEQUENCE: 11

Met Ser Ser Lys Pro Lys Ser Leu Glu Ile Ile Gly Ala Pro Phe Ser
1               5                   10                  15

Lys Gly Gln Pro Arg Gly Gly Val Glu Lys Gly Pro Ala Ala Leu Arg
            20                  25                  30

Lys Ala Gly Leu Leu Glu Lys Leu Lys Glu Thr Glu Tyr Asp Val Arg
        35                  40                  45

Asp His Gly Asp Leu Ala Phe Val Asp Val Pro Asn Asp Ser Ser Phe
    50                  55                  60

Gln Ile Val Lys Asn Pro Arg Ser Val Gly Lys Ala Asn Glu Glu Leu
65                  70                  75                  80

Ala Gly Val Val Ala Glu Val Gln Lys Asn Gly Arg Val Ser Val Val
                85                  90                  95

Leu Gly Gly Asp His Ser Leu Ala Val Gly Ser Ile Ser Gly His Ala
            100                 105                 110

Arg Val His Pro Asp Leu Cys Val Ile Trp Val Asp Ala His Thr Asp
        115                 120                 125

Ile Asn Thr Pro Leu Thr Thr Ser Ser Gly Asn Leu His Gly Gln Pro
    130                 135                 140

Val Ser Phe Leu Leu Lys Glu Leu Lys Gly Lys Phe Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Ile Lys Thr
            180                 185                 190

Leu Gly Ile Lys Tyr Phe Ser Met Thr Glu Val Asp Lys Leu Gly Ile
        195                 200                 205

Gly Lys Val Met Glu Glu Thr Phe Ser Tyr Leu Leu Gly Arg Lys Lys
    210                 215                 220

Arg Pro Ile His Leu Ser Phe Asp Val Asp Gly Leu Asp Pro Ala Phe
225                 230                 235                 240

Thr Pro Ala Thr Gly Thr Pro Val Leu Gly Gly Leu Ser Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Thr Leu Gly Lys Thr Ala Glu Glu
        275                 280                 285

Val Lys Ser Thr Val Asn Thr Ala Val Ala Leu Thr Leu Ala Cys Phe
    290                 295                 300

Gly Thr Gln Arg Glu Gly Asn His Lys Pro Gly Thr Asp Tyr Leu Lys
305                 310                 315                 320
```

```
Pro Pro Lys

<210> SEQ ID NO 12
<211> LENGTH: 50
<212> TYPE: PRT
<213> ORGANISM: Artificial Sequence
<220> FEATURE:
<223> OTHER INFORMATION: Peptide fragment of human Arginase 1

<400> SEQUENCE: 12

Gly Phe Ser Trp Val Thr Pro Cys Ile Ser Ala Lys Asp Ile Val Tyr
1               5                   10                  15

Ile Gly Leu Arg Asp Val Asp Pro Gly Glu His Tyr Ile Leu Lys Thr
            20                  25                  30

Leu Gly Ile Lys Tyr Phe Ser Met Thr Glu Val Asp Arg Leu Gly Ile
        35                  40                  45

Gly Lys
    50

<210> SEQ ID NO 13
<211> LENGTH: 50
<212> TYPE: PRT
<213> ORGANISM: Artificial Sequence
<220> FEATURE:
<223> OTHER INFORMATION: Peptide fragment of murine Arginase 1

<400> SEQUENCE: 13

Gly Phe Ser Trp Val Thr Pro Cys Ile Ser Ala Lys Asp Ile Val Tyr
1               5                   10                  15

Ile Gly Leu Arg Asp Val Asp Pro Gly Glu His Tyr Ile Ile Lys Thr
            20                  25                  30

Leu Gly Ile Lys Tyr Phe Ser Met Thr Glu Val Asp Lys Leu Gly Ile
        35                  40                  45

Gly Lys
    50
```

ARGINASE1 POLYPEPTIDES

CROSS-REFERENCE TO RELATED APPLICATIONS

This application is a U.S. National Phase application, filed under 35 U.S.C. § 371 (c), of International Application No. PCT/EP2019/075731, filed Sep. 24, 2019, which claims priority to, and the benefit of, United Kingdom Patent Application No. 1815549.9, filed Sep. 24, 2018. Each of these documents is incorporated by reference herein in its entirety for all purposes.

DESCRIPTION OF THE TEXT FILE SUBMITTED ELECTRONICALLY

The contents of the electronic sequence listing (IOBT_007_01US_SeqList_ST25.TXT; Size: 10,773 bytes; and Date of Creation: Nov. 1, 2024) are herein incorporated by reference in its entirety.

FIELD OF THE INVENTION

The present invention relates to novel polypeptides, which are derived from Arginase 1. The invention also relates to polynucleotides encoding the polypeptides. The invention also relates to compositions comprising the polypeptides and polynucleotides. The invention also concerns uses of the polypeptides, polynucleotides, and compositions.

BACKGROUND OF THE INVENTION

Arginase is an enzyme that catalyses a reaction which converts the amino acid L-arginine into L-ornithine and urea. This depletes the microenvironment of arginine and leads to a suppression of tumor-specific cytotoxic T-cell responses. Increased Arginase activity has been detected in the cancer cells of patients with breast, lung, colon or prostate cancer. It has been shown both in vitro and in vivo that mouse macrophages transfected with a rat Arginase gene promote the proliferation of co-cultured tumour cells. Furthermore induction of Arginase expression by macrophages has been shown to increase tumour vascularization through polyamine synthesis. The results of a murine lung carcinoma model showed that there existed a subpopulation of mature tumor-associated myeloid cells that expressed high levels of Arginase. These tumor-associated myeloid cells depleted the extracellular L-Arginine which inhibited antigen-specific proliferation of the tumor infiltrating lymphocytes (TILs). Injection of an Arginase inhibitor blocked the growth of the lung carcinoma in the mice. This shows how induction of Arginase expression in tumor cells and tumor associated myeoloid cells might promote tumor growth by suppression of the anti-tumor immune responses through negative effects on TILs.

MDSCs (myeloid-derived suppressor cells) inhibit the activation, proliferation, and cytotoxicity of effector T cells and natural killer cells, as well as induce Treg differentiation and expansion. Both cancer cells and MDSCs can suppress T cells by manipulating L-arginine metabolism via the enzymes nitric-oxide synthase (NOS) and arginase. Many tumours exhibit increased expressions of arginase and inducible NOS (iNOS), leading to arginine depletion from the tumour microenvironment. Several studies emphasize the importance of this altered tumour arginine metabolism in the suppression of tumour-specific T-cell responses, and it was recently demonstrated that Acute Myeloid Leukemia (AML) blasts show an arginase-dependent ability to inhibit T-cell proliferation and hematopoietic stem cells. Furthermore, arginase and iNOS inhibitors reduce the suppressive activity of AML.

SUMMARY OF THE INVENTION

The present inventors have previously identified a 50 amino acid region of Arginase 1 which is a "hot spot" for immunogenicity. This region corresponds to positions 161-210 of full length human Arginase 1 (SEQ ID NO: 10). The region and peptides derived from it are described in WO2018065563. (Note that the terms "Arginase 1", "Arg1", "Arginase1" are used interchangeably herein).

The present inventors have now identified that a specific sub-set of polypeptides derived from this region are particularly effective at stimulating immune responses. The polypeptides of the present invention are thus expected to be particularly effective at stimulating a beneficial immune response against Arginase 1 and Arginase 1-expressing cells. The development of novel immune therapies for cancer requires a thorough understanding of the molecules that are involved in the pathogenesis as well as the specific proteins recognized by the immune system. In the clinical setting the induction of Arginase specific immune responses could in addition to the killing of cancer cells support anti-cancer immune responses in general by suppressing the immune suppressive function of Arginase expressing cells especially MDSC and tumor-associated macrophages (TAMs). Hence, since Arginase-expressing cells antagonize the desired effects of other immunotherapeutic approaches targeting myeloid dendritic cells e.g. by vaccination with the polypeptides of the present invention, would consequently be highly synergistic with additional anti-cancer immunotherapy.

The present invention provides:
An isolated polypeptide consisting of any one of the following amino acid sequences:

```
                                       (SEQ ID NO: 1)
a. ISAKDIVYIGLRDVDPGEHYILKTLGIKYFSMTEVDRL;

(SEQ ID NO: 2)
b. ISAKDIVYIGLRDVDPGEHYIIKTLGIKYFSMTEVDKL;

(SEQ ID NO: 3)
c. ISAKDIVYIGLRDVDPGEHYILKTLGIKYFSM;

(SEQ ID NO: 4)
d. ISAKDIVYIGLRDVDPGEHYIIKTLGIKYFSM;

(SEQ ID NO: 5)
e. ISAKDIVYIGLRDVDPGEHYILKTLGIKYFSMTEVDRLGIGK;

(SEQ ID NO: 6)
f. ISAKDIVYIGLRDVDPGEHYIIKTLGIKYFSMTEVDKLGIGK.
```

The present invention further provides a polynucleotide encoding a polypeptide of the invention, optionally comprised within a vector.

The present invention also provides a composition comprising a polypeptide or polynucleotide of the invention, at least one pharmaceutically acceptable diluent, carrier or preservative, and optionally an adjuvant.

The present invention also provides a method of treating or preventing a disease or condition in a subject, the method comprising administering to the subject a polypeptide, polynucleotide, or a composition of the invention.

3

IFNγ ELISPOT responses against ArgLong, ArgLong2 and ArgLong3 peptides in PBMCS from four healthy donors (HD). Bars represent the mean number of spots per well+ standard error of the mean. Corresponding ELISPOT well images with and without the addition of peptides are also shown for each donor. Experiments were performed with $5 \times 10^5$ PBMCs/well in triplicates. TNTC—too numerous to count. *—p≤0.05 according to the distribution free resampling (DFR) rule.

Figure 2:
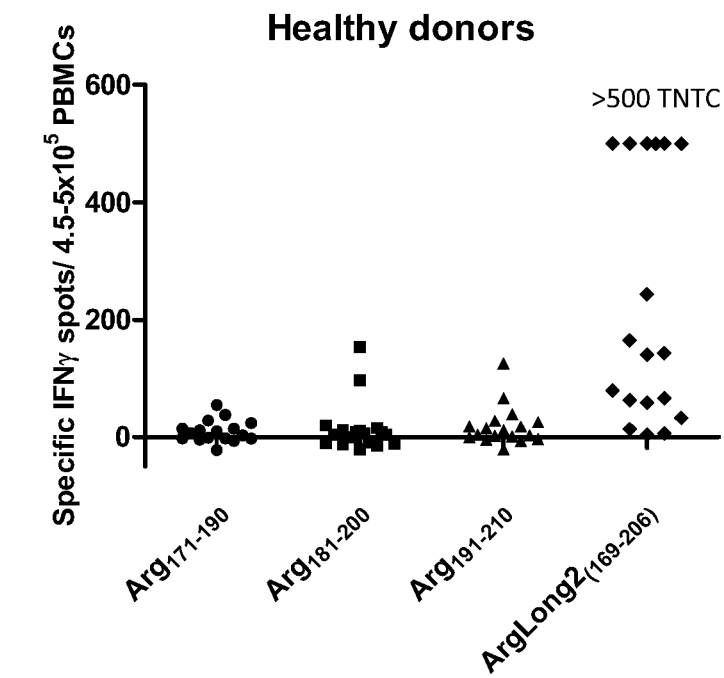
Figure 2:
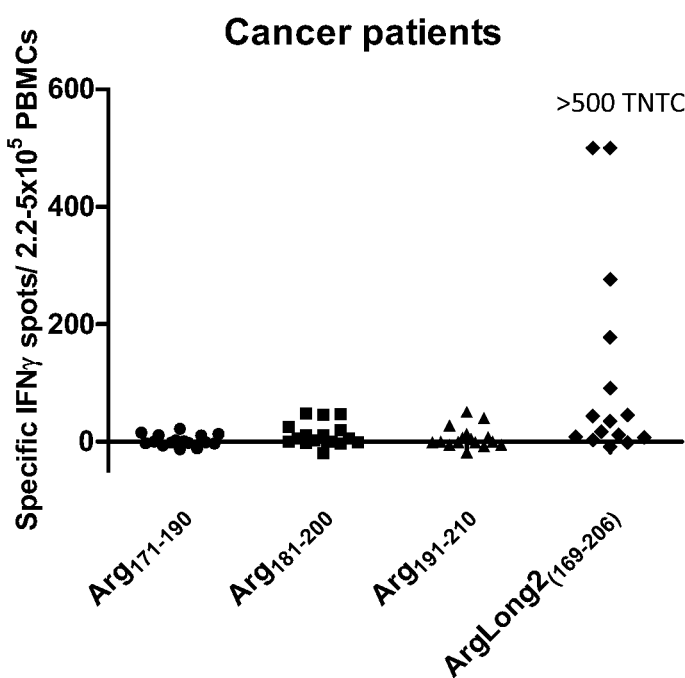

FIG. 2 shows responses against ArgLong2 compared to 20-mer peptides

IFNγ ELISPOT responses against $Arg_{171-190}$, $Arg_{181-200}$, $Arg_{191-210}$ and ArgLong2 in 19 healthy donors (top) and 16 cancer patients (bottom). Each dot represents an average number of peptide specific spots for a single patient/donor. Responses were calculated by subtracting the average spot count in control wells from the average spot count in peptide stimulated wells. Experiments performed with $4.5$-$5 \times 10^5$ PBMCs/well for healthy donors and $2.2$-$5 \times 10^5$ PBMCs/well for cancer patients, in triplicates or duplicates. Responses against ArgLong2 were too numerous to count (TNTC) in six healthy donors and 2 cancer patients and set to be >500 spots.

Figure 3A:
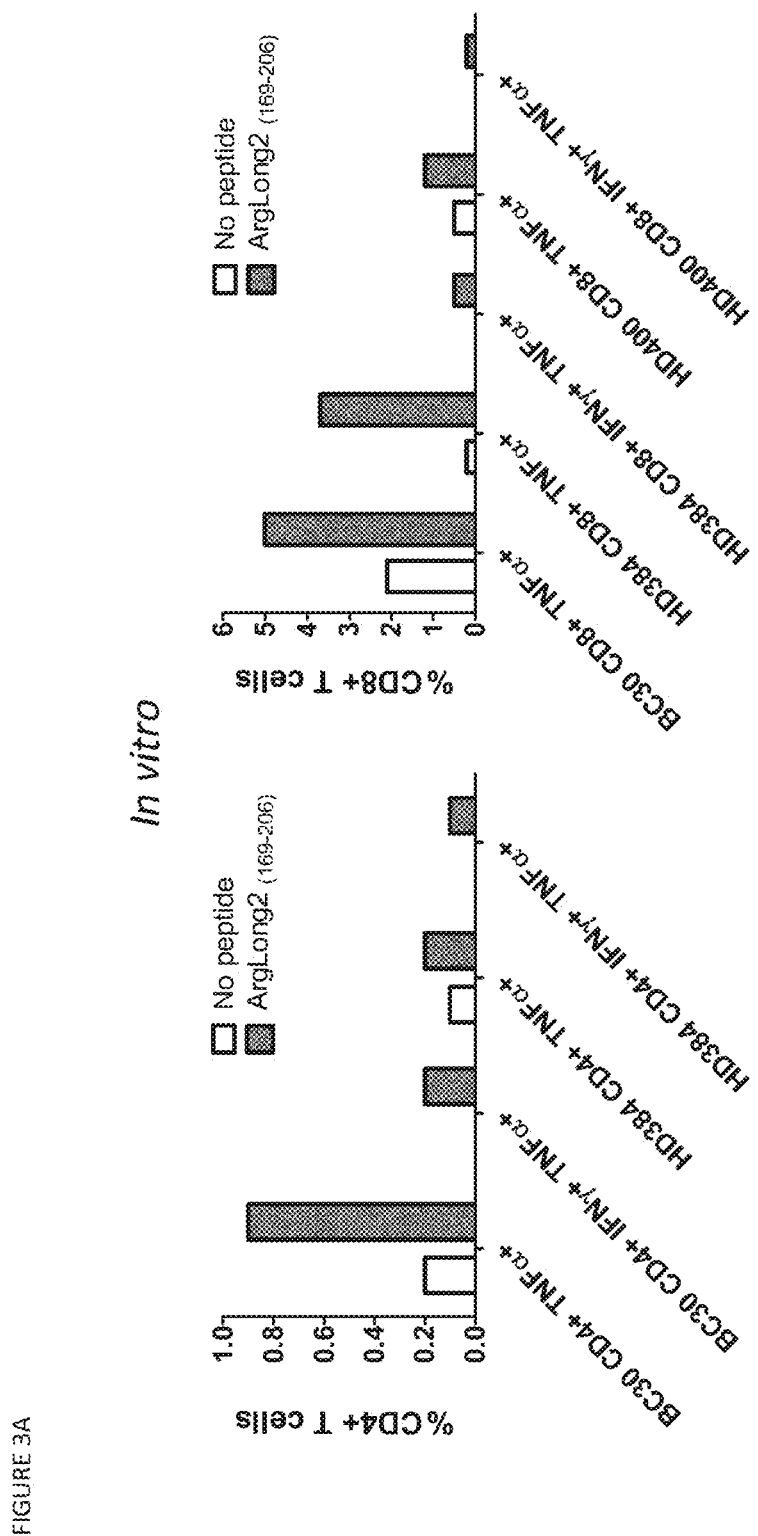

FIG. 3 shows CD4+ and CD8+ T cells respond to ArgLong2 in vitro and ex vivo

3A—In vitro responses against ArgLong2 in CD4+ (left) and CD8+ (right) T cells in intracellular staining of PBMCs from two healthy donors and one breast cancer patient. PBMCs were stimulated with ArgLong2 and low dose IL-2 for one week prior to ELISPOT assay.

3B—Ex vivo responses against ArgLong2 in CD4+ (left) and CD8+ (right) T cells in intracellular staining of PBMCs from two cancer patients, without prior stimulation (BC-breast cancer, MM-malignant melanoma).

Figure 4:
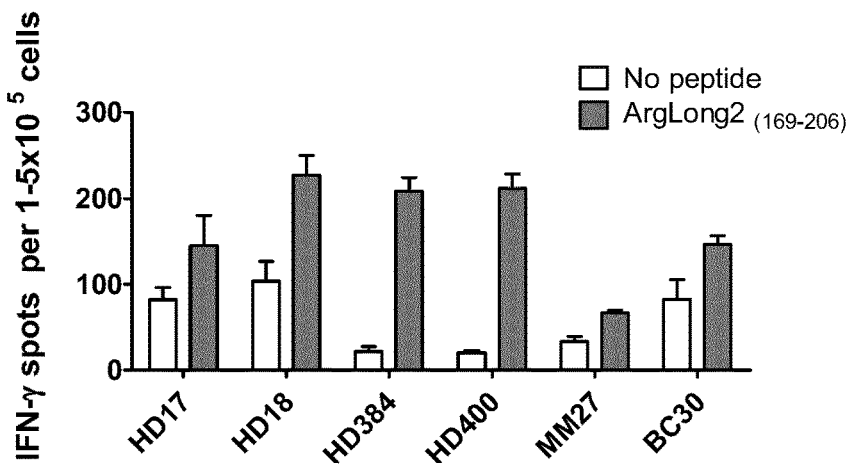
Figure 4:
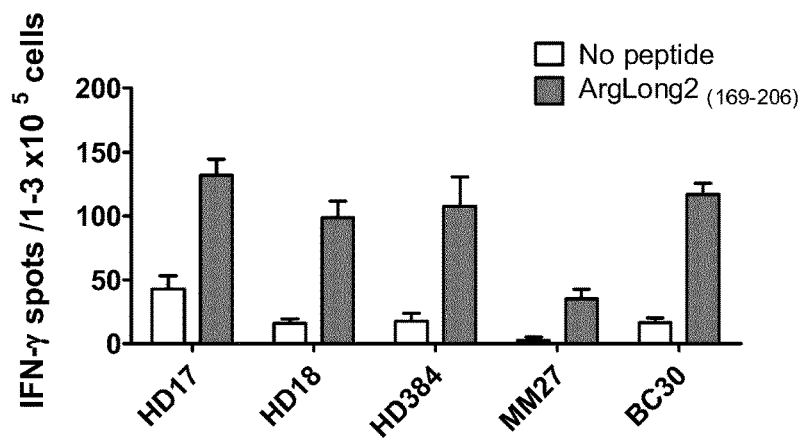
Figure 4:
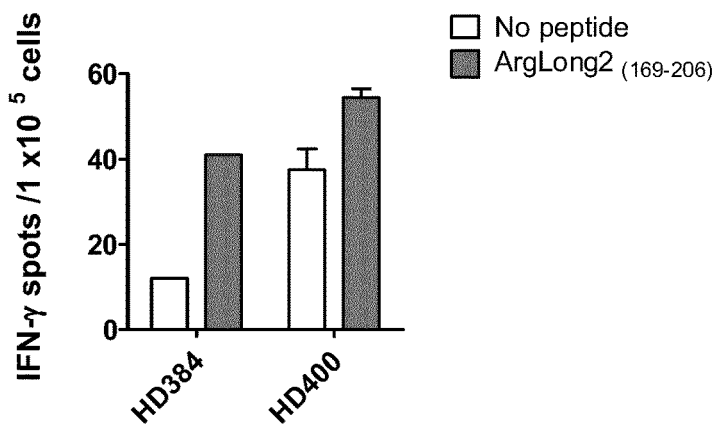

FIG. 4 shows ArgLong2 specific CD4+ and CD8+ cells are memory T cells

4A—Ex vivo responses against ArgLong2 in four healthy donors (HD) and two cancer patients (BC-breast cancer, MM-malignant melanoma). Experiment performed in triplicates with $1$-$5 \times 10^5$ cells/well.

4B—Ex vivo IFNγ ELISPOT of sorted CD4+ memory T cells (CD45RO+) from PBMCs of four healthy donors and two cancer patients (breast cancer and malignant melanoma).

Experiment performed in triplicates with $1$-$3 \times 10^5$ cells/well.

4C—Ex vivo IFNγ ELISPOT of sorted CD8+ memory T cells (CD45RO+) from PBMCs of two healthy donors. Experiment performed in duplicates or singlets with $1 \times 10^5$ cells/well. Bars represent average spot counts in peptide stimulated and controls wells+SEM.

Figure 5:
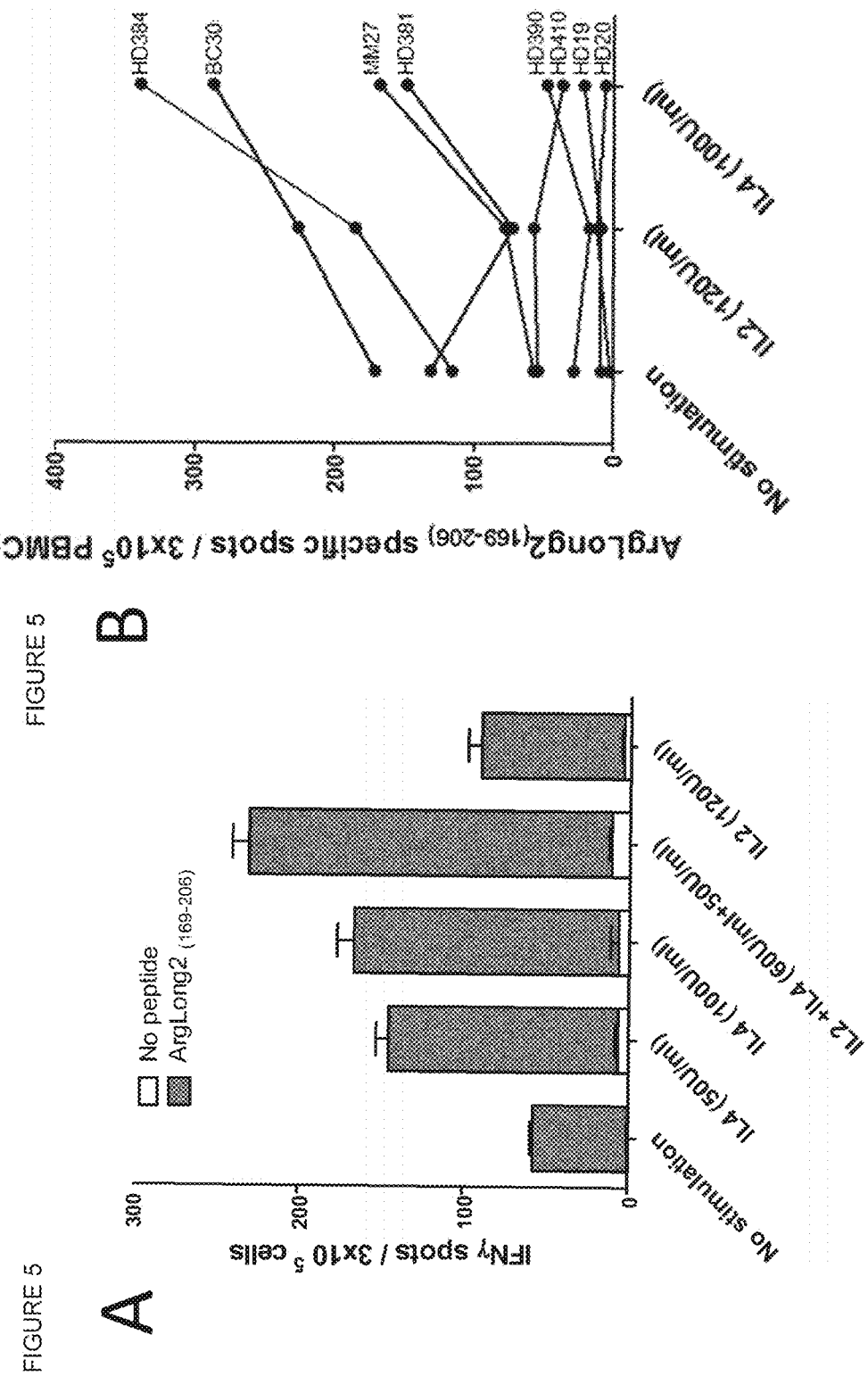

FIG. 5 shows IL-4 stimulation activates ArgLong2 specific T cells

A—IFNγ ELISPOT for ArgLong2 responses in melanoma patient PBMCs stimulated with IL-4 and/or IL-2 for one week. Non-stimulated PBMCs used as control. Superimposed bars show the mean spot counts of control and peptide stimulated wells+SEM. Experiment performed in triplicates with $3 \times 10^5$ cells/well. B—ArgLong2 specific responses in PBMCs from six healthy donors (HD) and two cancer patients (BC—breast cancer, MM—malignant melanoma) after stimulation with IL-2 (120 U/ml) or IL-4 (100 U/ml) for one week. Cells without cytokine stimulation used as control. Responses calculated as the difference in mean spot counts between peptide stimulated and control wells in ELISPOT. Experiment performed in triplicates or duplicates with $3 \times 10^5$ cells/well.

Figure 6:
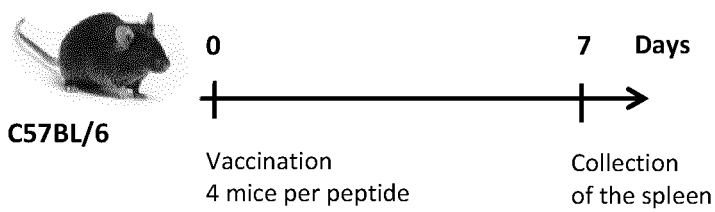
Figure 6:
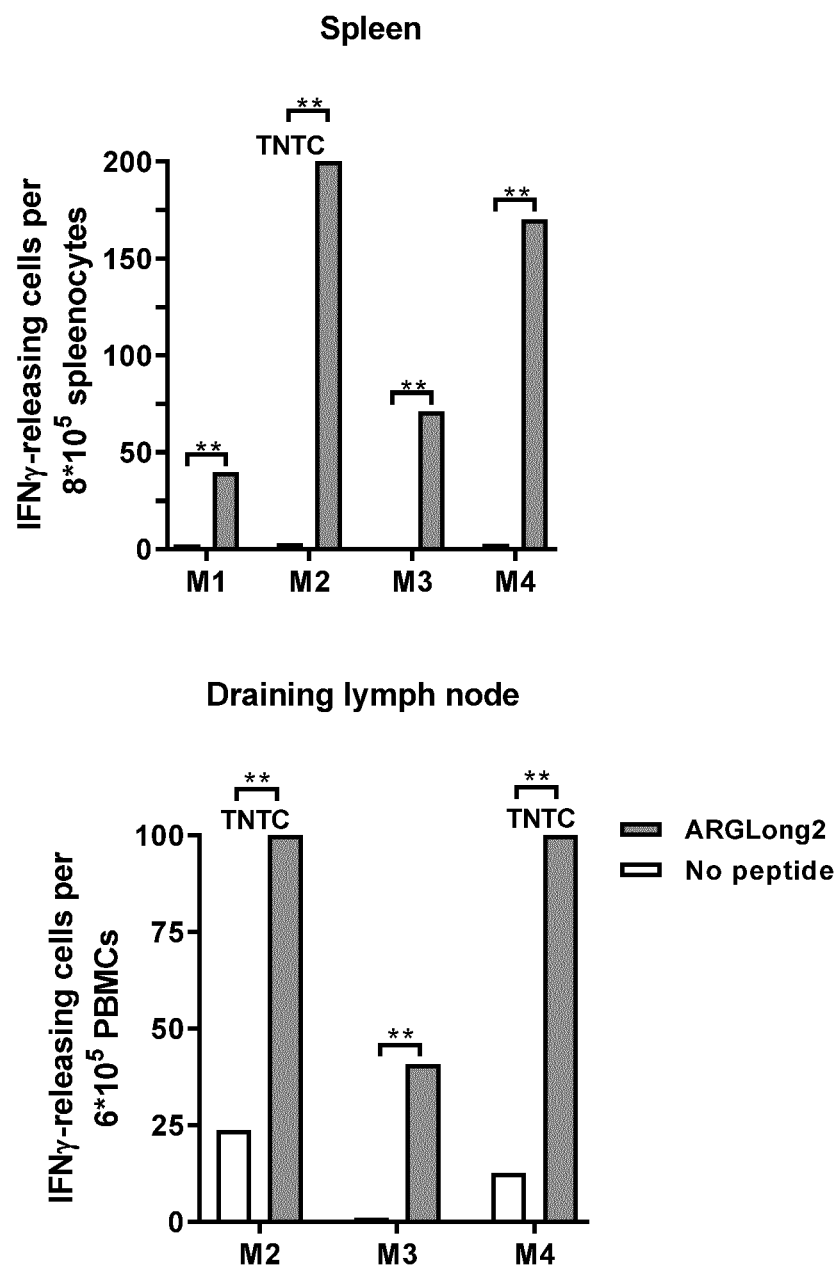

FIG. 6 shows ArgLong2-specific IFNγ immune responses mounted in vivo after immunization Four mice were vaccinated with ArgLong2 peptide and the immune response developed against the peptide was evaluated after 7 days by IFNγ ELISPOT. Cells from the spleen and draining lymph nodes from individual mice were subjected to ELISPOT assay. Bars represent the mean number of spots. ELISPOT were performed in triplicates with and without addition of the ArgLong2 peptide. "TNTC" denotes too numerous to count. ** denotes p<0.01 according to the distribution-free resampling method (DFR).

Figure 7:
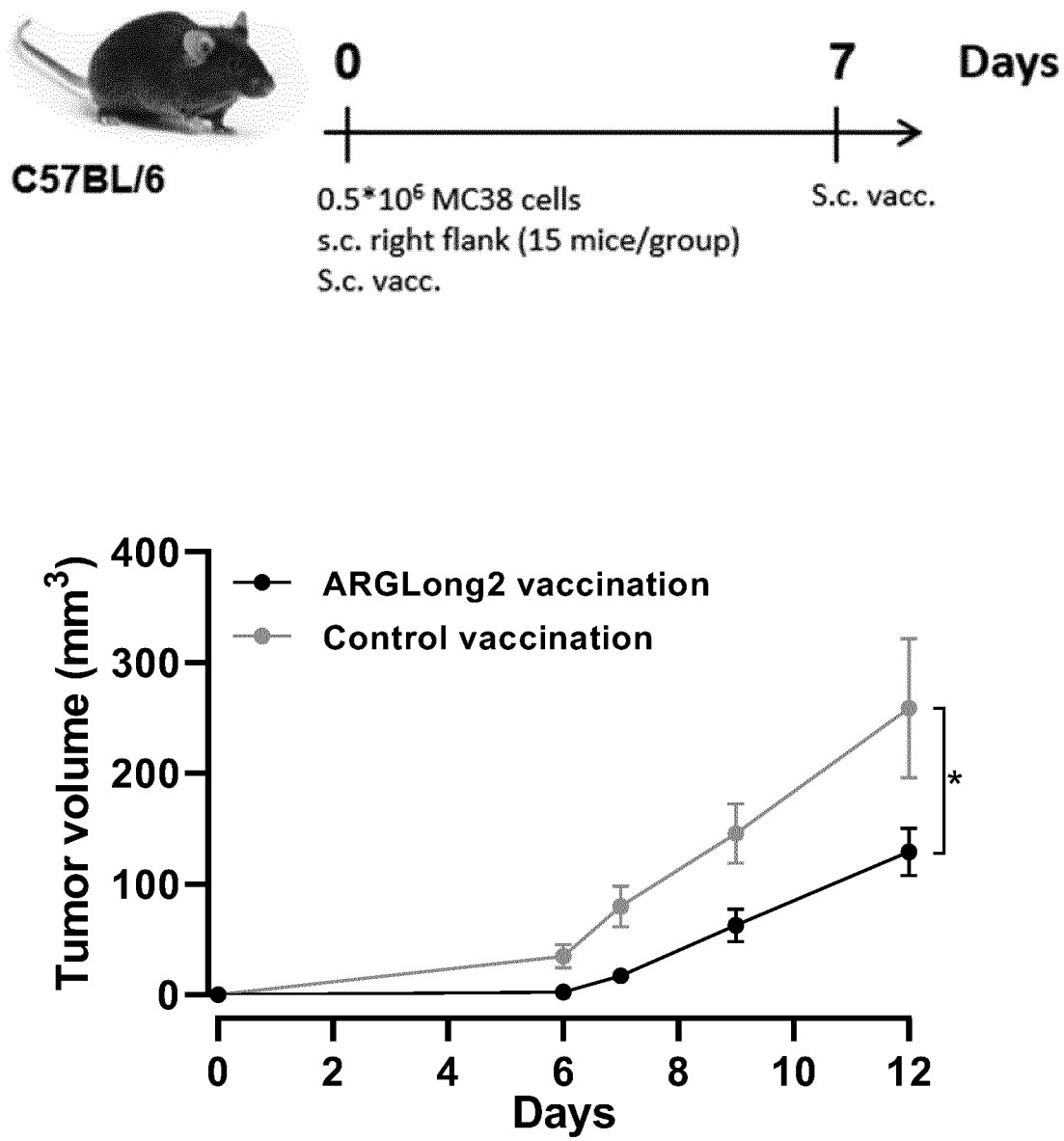

FIG. 7 shows ArgLong2 vaccination induces anti-tumour effects in the MC38 colon adenocarcinoma tumour model $0.5 \times 10^6$ MC38 tumour cells were inoculated subcutaneously on the right flank of 30 mice on day 0. On the same day vaccinations were initiated. The 15 mice in the treatment group were treated with 100 μg of ArgLong2 in emulsion with Montanide, and the 15 mice in the control group were treated with $H_2O$ in emulsion with Montanide. p=0.030 according to the Mixed effects analysis.

Figure 8:
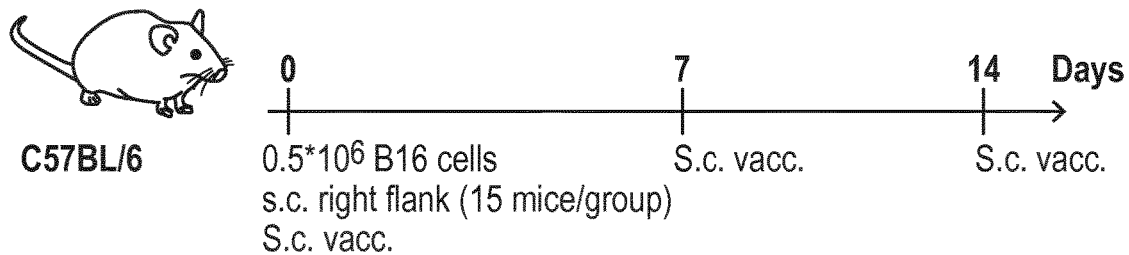
Figure 8:
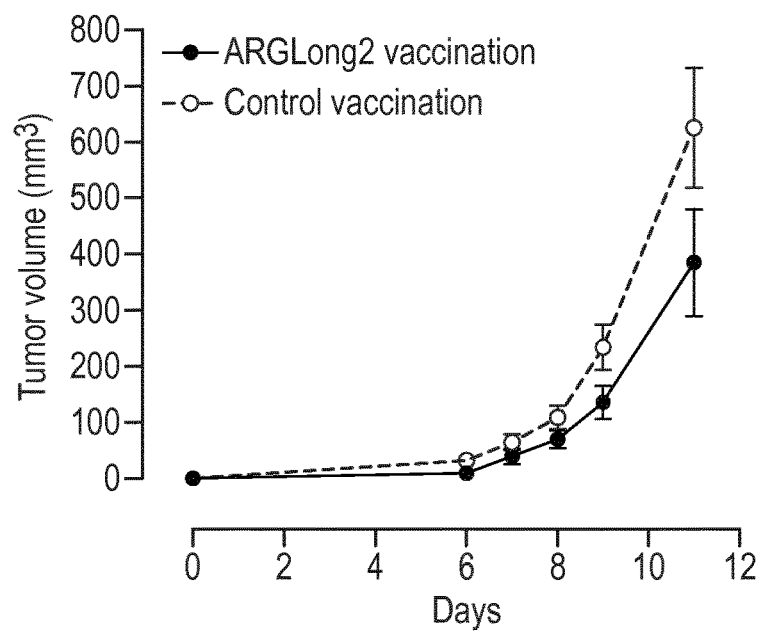
Figure 8:
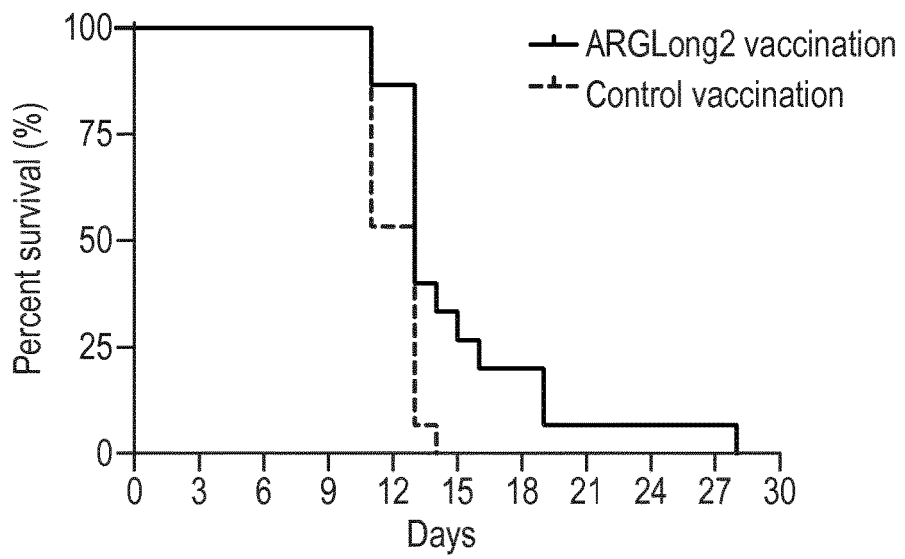

FIG. 8 shows ArgLong2 vaccination induces anti-tumour effects in the B16F10 melanoma tumour model $0.5 \times 10^6$ Bl6F10 tumour cells were inoculated subcutaneously on the right flank of 30 mice on day 0. On the same day vaccinations were initiated. The 15 mice in the treatment group were treated with 100 μg of ArgLong2 in emulsion with Montanide, and the 15 mice in the control group were treated with $H_2O$ in emulsion with Montanide. After three vaccinations the treatment were stopped. Mice were euthanized when the tumour volume exceeded 864 $mm^3$.

FIG. 9 shows ArgLong2-specific T cell clones recognizes Arginase 1-expressing THP-1 cells A and B—ArgLong2-specific CD4 T cell clone recognizes THP-1 cells when the Arginase 1 expression is induced by Th2 cytokine, quantified by intracellular cytokine staining. C—qPCR data showing that IL-13 pre-stimulation of THP-1 cells induces Arginase 1 expression.

Figure 10:
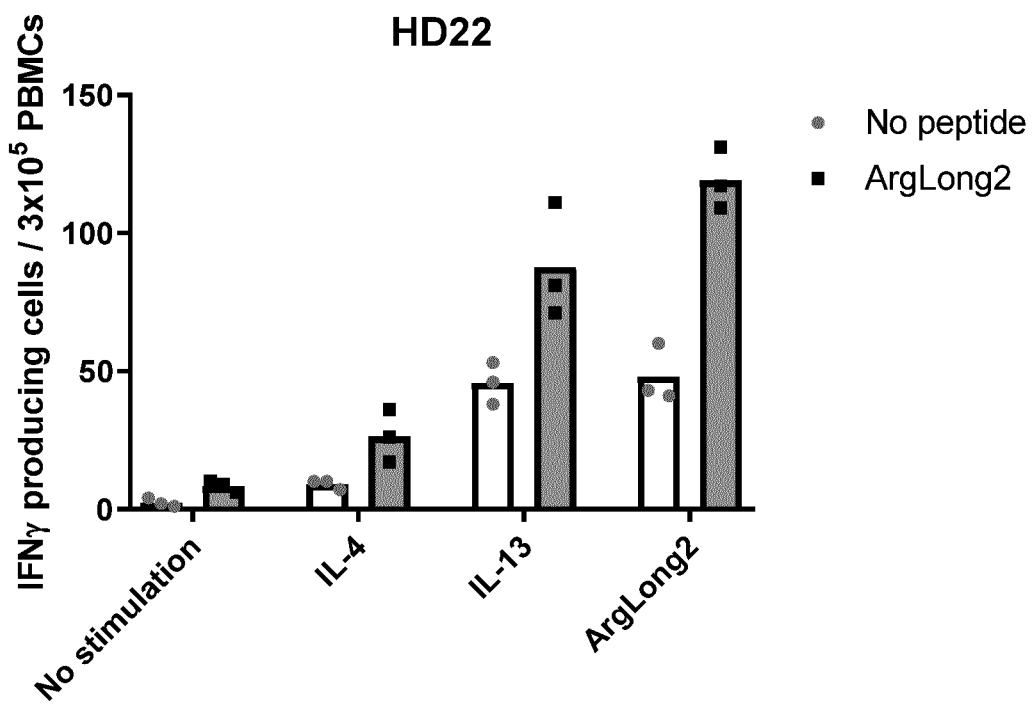

FIG. 10 shows in vitro cytokine stimulation alone is sufficient to expand T cell responses to ArgLong2 epitope PBMCs were treated with either Arginase 1-inducing Th2 cytokine (IL-4/IL-13) or ArgLong2 peptide for 7 days before ArgLong2-specific T cells were quantified in vitro by IFNγ ELISPOT.

BRIEF DESCRIPTION OF THE SEQUENCES

SEQ ID NOs: 1-9 are each an amino acid sequence of a polypeptide derived from the region corresponding to positions 161-210 of full length human Arginase 1 or murine Arginase 1.

SEQ ID NOs: 10 and 11 are the amino acid sequences of full length human Arginase 1 and murine Arginase 1, respectively.

SEQ ID NO: 12 is the amino acid sequence of the region corresponding to positions 161-210 of full length human Arginase 1.

SEQ ID NO: 13 is the amino acid sequence of the region corresponding to positions 161-210 of full length murine Arginase 1.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polypeptide" includes "polypeptides", and the like.

A "polypeptide" is used herein in its broadest sense to refer to a compound of two or more subunit amino acids, amino acid analogs, or other peptidomimetics. The term "polypeptide" thus includes short peptide sequences and also longer polypeptides and proteins. As used herein, the term "amino acid" refers to either natural and/or unnatural or synthetic amino acids, including both D or L optical isomers, and amino acid analogs and peptidomimetics.

The terms "patient" and "subject" are used interchangeably and typically refer to a human.

All publications, patents and patent applications cited herein, whether supra or infra, are hereby incorporated by reference in their entirety.

The present inventors have previously identified a 50 amino acid region of human and murine Arginase 1 which is a "hot spot" for immunogenicity. This region corresponds to positions 161-210 of full length human Arginase 1 (SEQ ID NO: 10) or full length murine Arginase 1 (SEQ ID NO: 11). The region and peptide fragments derived from it are described in WO2018065563. The present inventors have now identified that a polypeptide consisting of a specific contiguous amino acid sequence of this region is surprisingly immunogenic relative to other amino acid sequences from the same region.

By "immunogenic" herein it is meant that a polypeptide is capable of eliciting an immune response to the Arginase 1 protein, preferably when said protein is present in or on cells expressing the Arginase 1 protein. In other words, the polypeptide may be described as immunogenic to Arginase 1. The polypeptide may alternatively be described as an immunogenic fragment of Arginase 1. The immune response is preferably a T cell response. The immune response may be detected in at least one individual (or in sample taken from the individual) after administration of the polypeptide to said individual (or said sample).

A polypeptide may be identified as immunogenic using any suitable method, including in vitro methods. For example, a peptide may be identified as immunogenic if it has at least one of the following characteristics:
(i) It is capable of eliciting IFN-γ-producing cells in a PBL population of a healthy subject and/or a cancer patient as determined by an ELISPOT assay, and/or
(ii) It is capable of in situ detection in a sample of tumor tissue of CTLs that are reactive with Arginase 1; and/or
(iii) It is capable of inducing the in vitro growth of specific T-cells.

Methods suitable for determining whether a polypeptide is immunogenic active are also described in the Examples section below.

The polypeptide of the invention may consist of:
the amino acid sequence corresponding to positions 169-206 of full length human Arginase 1. This polypeptide may be referred to herein as ArgLong2. Its sequence is provided as SEQ ID NO: 1.
the amino acid sequence corresponding to positions 169-206 of full length murine Arginase 1. This polypeptide may be referred to herein as mArgLong2. Its sequence is provided as SEQ ID NO: 2.
the amino acid sequence corresponding to positions 169-200 of full length human Arginase 1. This polypeptide may be referred to herein as ArgLong3. Its sequence is provided as SEQ ID NO: 3.
the amino acid sequence corresponding to positions 169-200 of full length murine Arginase 1. This polypeptide may be referred to herein as mArgLong3. Its sequence is provided as SEQ ID NO: 4.
the amino acid sequence corresponding to positions 169-210 of full length human Arginase 1. This polypeptide may be referred to herein as ArgLong. Its sequence is provided as SEQ ID NO: 5.
the amino acid sequence corresponding to positions 169-210 of full length murine Arginase 1. This polypeptide may be referred to herein as mArgLong. Its sequence is provided as SEQ ID NO: 6.

The polypeptide preferably consists of the amino acid sequence of corresponding to positions 169-206 of full length human or murine Arginase 1, that is it consist of the amino acid sequence of SEQ ID NO: 1 or 2. That is, the polypeptide is preferably ArgLong2 or mArgLong2.

The polypeptide most preferably consists of the amino acid sequence of corresponding to positions 169-206 of full length human Arginase 1, that is it consists of the amino acid sequence of SEQ ID NO: 1. That is, the polypeptide is preferably ArgLong2.

In any polypeptide described herein, the amino acid sequence may be modified by one, two, three, four, or five (that is up to five) additions, deletions or substitutions, provided that a polypeptide having the modified sequence exhibits the same or increased immunogenicity to Arginase 1, as compared to a polypeptide having the unmodified sequence. By "the same" it is to be understood that the polypeptide of the modified sequence does not exhibit significantly reduced immunogenicity to Arginase 1 as compared to polypeptide of the unmodified sequence. Any comparison of immunogenicity between sequences is to be conducted using the same assay. Unless otherwise specified, modifications to a polypeptide sequence are preferably conservative amino acid substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table A1 below. Where amino acids have similar polarity, this can be determined by reference to the hydropathy scale for amino acid side chains in Table A2.

TABLE A1

Chemical properties of amino acids

| | | | |
|---|---|---|---|
| Ala (A) | aliphatic, hydrophobic, neutral | Met (M) | hydrophobic, neutral |
| Cys (C) | polar, hydrophobic, neutral | Asn (N) | polar, hydrophilic, neutral |
| Asp (D) | polar, hydrophilic, charged (−) | Pro (P) | hydrophobic, neutral |
| Glu (E) | polar, hydrophilic, charged (−) | Gln (Q) | polar, hydrophilic, neutral |

TABLE A1-continued

Chemical properties of amino acids

| | | | |
|---|---|---|---|
| Phe (F) | aromatic, hydrophobic, neutral | Arg (R) | polar, hydrophilic, charged (+) |
| Gly (G) | aliphatic, neutral | Ser (S) | polar, hydrophilic, neutral |
| His (H) | aromatic, polar, hydrophilic, charged (+) | Thr (T) | polar, hydrophilic, neutral |
| Ile (I) | aliphatic, hydrophobic, neutral | Val (V) | aliphatic, hydrophobic, neutral |
| Lys (K) | polar, hydrophilic, charged (+) | Trp (W) | aromatic, hydrophobic, neutral |
| Leu (L) | aliphatic, hydrophobic, neutral | Tyr (Y) | aromatic, polar, hydrophobic |

TABLE A2

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

In any polypeptide disclosed herein, any one or more of the following modifications may be made to improve physiochemical properties (e.g. stability), provided that the polypeptide exhibits the same or increased immunogenicity to Arginase 1, as compared to a polypeptide having the unmodified sequence:
 a) Replacement of the C terminal amino acid with the corresponding amide (may increase resistance to carboxypeptidases);
 b) Replacement of the N terminal amino acid with the corresponding acylated amino acid (may increase resistance to aminopeptidases);
 c) Replacement of one or more amino acids with the corresponding methylated amino acids (may improve proteolytic resistance);
 d) Replacement of one or more amino acids with the corresponding amino acid in D-configuration (may improve proteolytic resistance).

For the modification of types (c) and (d), a preferred example is the modification of the Tyr residue in the position corresponding to position 29 of SEQ ID NO: 1 (e.g. replace with N-methyl(Tyr) or replace with D configuration Tyr). This is because the Tyr appears immediately following a Lys residue at position 28, and is thus at a potential site for proteolysis by Trypsin-like proteases (which typically cleave after Lys).

Any polypeptide disclosed herein may have attached at the N and/or C terminus at least one additional moiety to improve solubility, stability and/or to aid with manufacture/isolation, provided that the polypeptide exhibits the same or increased immunogenicity to Arginase 1, as compared to a polypeptide lacking the additional moiety. Suitable moieties include hydrophilic amino acids. For example, the amino acid sequences KK, KR or RR may be added at the N terminus and/or C terminus. Other suitable moieties include Albumin or PEG (Polyethylene Glycol).

A polypeptide as disclosed herein may be produced by any suitable means. For example, the polypeptide may be synthesised directly using standard techniques known in the art, such as Fmoc solid phase chemistry, Boc solid phase chemistry or by solution phase peptide synthesis. Alternatively, a polypeptide may be produced by transforming a cell, typically a bacterial cell, with a nucleic acid molecule or vector which encodes said polypeptide. The invention provides nucleic acid molecules and vectors which encode a polypeptide of the invention. The invention also provides a host cell comprising such a nucleic acid or vector.

The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or substantially isolated form. By substantially isolated, it is meant that there may be substantial, but not total, isolation of the polypeptide from any surrounding medium. The polynucleotides may be mixed with carriers or diluents which will not interfere with their intended use and still be regarded as substantially isolated. A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences, for example in an expression vector. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Polynucleotides can be synthesised according to methods well known in the art, as described by way of example in Sambrook et al (1989, Molecular Cloning—a laboratory manual; Cold Spring Harbor Press). The nucleic acid molecules of the present invention may be provided in the form of an expression cassette which includes control sequences operably linked to the inserted sequence, thus allowing for expression of the polypeptide of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject.

Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

The invention also includes cells that have been modified to express a polypeptide of the invention. Such cells typically include prokaryotic cells such as bacterial cells, for example E. coli. Such cells may be cultured using routine methods to produce a polypeptide of the invention.

The polypeptide of the invention may be in a substantially isolated form. It may be mixed with carriers, preservatives, or diluents (discussed below) which will not interfere with the intended use, and/or with an adjuvant (also discussed below) and still be regarded as substantially isolated. It may also be in a substantially purified form, in which case it will generally comprise at least 90%, e.g. at least 95%, 98% or 99%, of the protein in the preparation.

Compositions Comprising Polypeptides or Polynucleotides

In another aspect, the present invention provides a composition comprising a polypeptide of the invention. The present invention also provides a composition comprising a polynucleotide encoding a polypeptide of the invention. For example, the invention provides a composition comprising one or more polypeptides of the invention, and at least one pharmaceutically acceptable carrier, preservative or excipient. Alternatively, the invention provides a composition comprising one or more polynucleotides encoding a polypeptide of the invention, and at least one pharmaceutically acceptable carrier, preservative or excipient. The carrier, preservative and excipient must be 'acceptable' in the sense of being compatible with the other ingredients of the composition and not deleterious to a subject to which the composition is administered. Typically, all components and the final composition are sterile and pyrogen free. The composition may be a pharmaceutical composition. The composition may preferably comprise an adjuvant.

Adjuvants are any substance whose admixture into the composition increases or otherwise modifies the immune response elicited by the composition. Adjuvants, broadly defined, are substances which promote immune responses. Adjuvants may also preferably have a depot effect, in that they also result in a slow and sustained release of an active agent from the administration site. A general discussion of adjuvants is provided in Goding, Monoclonal Antibodies: Principles & Practice (2nd edition, 1986) at pages 61-63.

Adjuvants may be selected from the group consisting of: A1K(SO4)2, AlNa(SO4)2, AlNH4 (SO4), silica, alum, Al(OH)3, Ca3 (PO4)2, kaolin, carbon, aluminum hydroxide, muramyl dipeptides, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), RIBI (MPL+TDM+CWS) in a 2% squalene/Tween-80® emulsion, lipopolysaccharides and its various derivatives, including lipid A, Freund's Complete Adjuvant (FCA), Freund's Incomplete Adjuvants, Merck Adjuvant 65, polynucleotides (for example, poly IC and poly AU acids), wax D from *Mycobacterium*, tuberculosis, substances found in *Corynebacterium parvum, Bordetella pertussis*, and members of the genus *Brucella*, Titermax, ISCOMS, Quil A, ALUN (see U.S. Pat. Nos. 58,767 and 5,554,372), Lipid A derivatives, choleratoxin derivatives, HSP derivatives, LPS derivatives, synthetic peptide matrixes or GMDP, Interleukin 1, Interleukin 2, Montanide ISA-51 and QS-21. Various saponin extracts have also been suggested to be useful as adjuvants in immunogenic compositions. Granulocyte-macrophage colony stimulating factor (GM-CSF) may also be used as an adjuvant.

Preferred adjuvants to be used with the invention include oil/surfactant based adjuvants such as Montanide adjuvants (available from Seppic, Belgium), preferably Montanide ISA-51. Other preferred adjuvants are bacterial DNA based adjuvants, such as adjuvants including CpG oligonucleotide sequences. Yet other preferred adjuvants are viral dsRNA based adjuvants, such as poly I:C. GM-CSF and Imidazochinilines are also examples of preferred adjuvants.

The adjuvant is most preferably a Montanide ISA adjuvant. The Montanide ISA adjuvant is preferably Montanide ISA 51 or Montanide ISA 720.

In Goding, Monoclonal Antibodies: Principles & Practice (2nd edition, 1986) at pages 61-63 it is also noted that, when an antigen of interest is of low molecular weight, or is poorly immunogenic, coupling to an immunogenic carrier is recommended. A polypeptide of the invention may therefore be coupled to a carrier. A carrier may be present independently of an adjuvant. The function of a carrier can be, for example, to increase the molecular weight of a polypeptide fragment in order to increase activity or immunogenicity, to confer stability, to increase the biological activity, or to increase serum half-life. Furthermore, a carrier may aid in presenting the polypeptide or fragment thereof to T-cells. Thus, in the composition, the polypeptide may be associated with a carrier such as those set out below.

The carrier may be any suitable carrier known to a person skilled in the art, for example a protein or an antigen presenting cell, such as a dendritic cell (DC). Carrier proteins include keyhole limpet hemocyanin, serum proteins such as transferrin, bovine serum albumin, human serum albumin, thyroglobulin or ovalbumin, immunoglobulins, or hormones, such as insulin or palmitic acid. Alternatively the carrier protein may be tetanus toxoid or diphtheria toxoid. Alternatively, the carrier may be a dextran such as sepharose. The carrier must be physiologically acceptable to humans and safe.

If the composition comprises an excipient, it must be 'pharmaceutically acceptable' in the sense of being compatible with the other ingredients of the composition and not deleterious to the recipient thereof. Auxiliary substances, such as wetting or emulsifying agents, pH buffering substances and the like, may be present in the excipient. These excipients and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Formulation of a suitable composition can be carried out using standard pharmaceutical formulation chemistries and methodologies all of which are readily available to the reasonably skilled artisan. Such compositions may be prepared, packaged, or sold in a form suitable for bolus administration or for continuous administration. Injectable compositions may be prepared, packaged, or sold in unit dosage form, such as in ampoules or in multi-dose containers optionally containing a preservative. Compositions include, but are not limited to, suspensions, solutions, emulsions in oily or aqueous vehicles, pastes, and implantable sustained-release or biodegradable formulations. In one embodiment of a composition, the active ingredient is provided in dry (for e.g., a powder or granules) form for reconstitution with a suitable vehicle (e. g., sterile pyrogen-free water) prior to administration of the reconstituted composition. The composition may be prepared, packaged, or sold in the form of a sterile injectable aqueous or oily suspension or solution. This suspension or solution may be formulated according to the known art, and may comprise, in addition to the active ingredient, additional ingredients such as the adjuvants, excipients and auxiliary substances described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt. Alternatively, the active ingredients of the composition may be encapsulated, adsorbed to, or associated with, particulate carriers. Suitable particulate carriers include those derived from polymethyl methacrylate polymers, as well as PLG microparticles derived from poly(lactides) and poly (lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules.

Methods of Use

The polypeptide, polynucleotide or composition of the invention may be used in a method of treating or preventing a disease or condition in a subject. The polypeptide, polynucleotide or composition of the invention may be used in the manufacture of a medicament for use in a method of treating or preventing a disease or condition in a subject. The method comprises administering to the said subject the said polypeptide, the said polynucleotide or the said composition. Administration may be of a therapeutically or prophylactically effective quantity of the said polypeptide, the said polynucleotide or the said composition, to a subject in need thereof.

The disease or condition may be characterized at least in part by inappropriate or excessive immune suppressive function of Arginase 1. The disease or condition may be a cancer, preferably a cancer which expresses Arginase 1 and/or which is associated with inappropriate or excessive immune suppressive function of Arginase 1. The cancer may be breast, lung, colon or prostate cancer, or may be a leukemia, preferably acute myeloid leukemia (AML), or may be a melanoma.

The method may comprise simultaneous or sequential administration with an additional cancer therapy. The additional cancer therapy may be selected from a cytokine therapy, a T-cell therapy, an NK therapy, an immune system checkpoint inhibitor, chemotherapy, radiotherapy, immunostimulating substances, gene therapy, or an antibody.

The antibody may be Abagovomab, Abciximab, Actoxumab, Adalimumab, Adecatumumab, Afelimomab, Afutuzumab, Alacizumab pegol, ALD518, Alemtuzumab, Alirocumab, Altumomab pentetate, Amatuximab, Anatumomab mafenatox, Anrukinzumab, Apolizumab, Arcitumomab, Aselizumab, Atinumab, Atlizumab (=tocilizumab), Atorolimumab, Bapineuzumab, Basiliximab, Bavituximab, Bectumomab, Belimumab, Benralizumab, Bertilimumab, Besilesomab, Bevacizumab, Bezlotoxumab, Biciromab, Bimagrumab, Bivatuzumab mertansine, Blinatumomab, Blosozumab, Brentuximab vedotin, Briakinumab, Brodalumab, Canakinumab, Cantuzumab mertansine, Cantuzumab ravtansine, Caplacizumab, Capromab pendetide, Carlumab, Catumaxomab, CC49, Cedelizumab, Certolizumab pegol, Cetuximab, Ch. 14.18, Citatuzumab bogatox, Cixutumumab, Clazakizumab, Clenoliximab, Clivatuzumab tetraxetan, Conatumumab, Concizumab, Crenezumab, CR6261, Dacetuzumab, Daclizumab, Dalotuzumab, Daratumumab, Demcizumab, Denosumab, Detumomab, Dorlimomab aritox, Drozitumab, Duligotumab, Dupilumab, Dusigitumab, Ecromeximab, Eculizumab, Edobacomab, Edrecolomab, Efalizumab, Efungumab, Elotuzumab Elsilimomab, Enavatuzumab, Enlimomab pegol, Enokizumab, Enoticumab, Ensituximab, Epitumomab cituxetan, Epratuzumab, Erlizumab, Ertumaxomab, Etaracizumab, Etrolizumab, Evolocumab, Exbivirumab, Fanolesomab, Faralimomab Farletuzumab, Fasinumab, FBTA05, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, GS6624, Ibalizumab, Ibritumomab tiuxetan, Icrucumab, Igovomab, Imciromab, Imgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lampalizumab, Lebrikizumab, Lemalesomab, Lerdelimumab, Lexatumumab, Libivirumab, Ligelizumab, Lintuzumab, Lirilumab, Lodelcizumab, Lorvotuzumab mertansine, Lucatumumab, Lumiliximab, Mapatumumab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Obinutuzumab, Ocaratuzumab, Ocrelizumab, Odulimomab, Ofatumumab, Olaratumab, Olokizumab, Omalizumab, Onartuzumab, Oportuzumab monatox, Oregovomab, Orticumab, Otelixizumab, Oxelumab, Ozanezumab, Ozoralizumab, Pagibaximab, Palivizumab, Panitumumab, Panobacumab, Parsatuzumab, Pascolizumab, Pateclizumab, Patritumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO 140, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Seribantumab, Setoxaximab, Sevirumab, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Teneliximab, Teplizumab, Teprotumumab, TGN1412, Ticilimumab (=tremelimumab), Tildrakizumab, Tigatuzumab, TNX-650, Tocilizumab (=atlizumab), Toralizumab, Tositumomab, Tralokinumab, Trastuzumab, TRBS07, Tregalizumab, Tremelimumab Tucotuzumab celmoleukin, Tuvirumab, Ublituximab, Urelumab, Urtoxazumab, Ustekinumab, Vapaliximab, Vatelizumab, Vedolizumab, Veltuzumab, Vepalimomab Vesencumab, Visilizumab, Volociximab, Vorsetuzumab mafodotin, Votumumab, Zalutumumab, Zanolimumab, Zatuximab, Ziralimumab or Zolimomab aritox.

Preferred antibodies include Natalizumab, Vedolizumab, Belimumab, Atacicept, Alefacept, Otelixizumab, Teplizumab, Rituximab, Ofatumumab, Ocrelizumab, Epratuzumab, Alemtuzumab, Abatacept, Eculizumab, Omalizumab, Canakinumab, Meplizumab, Reslizumab, Tocilizumab, Ustekinumab, Briakinumab, Etanercept, Inlfliximab, Adalimumab, Certolizumab pegol, Golimumab, Trastuzumab, Gemtuzumab, Ozogamicin, Ibritumomab, Tiuxetan, Tostitumomab, Cetuximab, Bevacizumab, Panitumumab, Denosumab, Ipilimumab, Brentuximab and Vedotin.

Particularly preferred antibodies that may be used in the method of the invention include: daratumumab, nivolumab, pembrolizumab, avelumab, rituximab, trastuzumab, pertuzumab, alemtuzumab, cetuximab, panitumumab, tositumomab and ofatumumab. Daratumumab is especially preferred.

The additional cancer therapy may be selected from the group consisting of Actimide, Azacitidine, Azathioprine, Bleomycin, Carboplatin, Capecitabine, Cisplatin, Chlorambucil, Cyclophosphamide, Cytarabine, Dauno-rubicin, Docetaxel, Doxifluridine, Doxorubicin, Epirubicin, Etoposide, Fludarabine, Fluor-ouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine.

The polypeptide or composition of the invention may also be used in a method of stimulating Arginase 1-specific T cells, such as CD4 and CD8 T-cells, comprising contacting cells with the said polypeptide or composition. The method may be conducted ex vivo. The cells may be present in a sample taken from a healthy subject or from a cancer patient, such as in a tumour sample.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

Example 1

Materials and Methods

Patient Material

PBMCs from healthy donors were isolated using density gradient separation over Lymphoprep™ (STEMCELL Technologies) and cryopreserved at −150° C. in FBS supplemented with 10% DMSO. PBMCs from cancer patients were isolated from blood sample a minimum of four weeks after the termination of any anti-cancer therapy. The protocol was approved by the Scientific Ethics Committee for The Capital Region of Denmark and conducted in accordance with the provisions of the Declaration of Helsinki. Written informed consent from the patients was obtained before study entry.

Peptides

Peptides were synthesized by standard methods and provided dissolved in DMSO to obtain a stock concentration of 10 mM. The sequences of the peptides used in these experiments are shown in full below in alignment with each other, and are also set out in the section entitled "Sequences"). Peptides are described by SEQ ID NO, by name, or by reference to the start and end positions of each peptide sequence within the full length sequence of Arginase 1. Each may be used interchangeably. For example, the peptide of SEQ ID NO: 1 may alternatively be referred to by the name ArgLong2, or may alternatively be referred to as Arg169-206 (given a start position of 169 and end position of 206). The intended reference in each case will be clear from the context.

```
Longer peptide sequences:
ArgLong:
ISAKDIVYIGLRDVDPGEHYILKTLGIKYFSMTEVDRLGIGK ArgLong2:
ISAKDIVYIGLRDVDPGEHYILKTLGIKYFSMTEVDRL ArgLong3:
ISAKDIVYIGLRDVDPGEHYILKTLGIKYFSM 20-mer peptides:
Arg171-190:
   AKDIVYIGLRDVDPGEHYIL Arg181-200:
             DVDPGEHYILKTLGIKYFSM Arg191-210:
                       KTLGIKYFSMTEVDRLGIGK
```

ELISPOT Assay

For in vitro ELISPOT, PBMCs from cancer patients and healthy donors were pulsed with 20 µM of Arginase 1-derived peptides and 120 U/ml IL-2 in 24-well plates for 7 days before being used in an ELISPOT assay. The cells were placed in 96-well nitrocellulose ELISPOT plates (MultiScreen MAIP N45; Millipore) pre-coated with IFNγ capture antibody (Mabtech). Arginase peptides added to a final concentration of 5 µM and plates incubated at 37° C. for 14-16 hours. After the incubation the cells were washed off and secondary biotinylated Ab (Mabtech, cat. 3420-6-1000) was added for 2 hours at room temperature. Unbound secondary antibody was washed off and streptavidin conjugated alkaline phosphatase (AP) (Mabtech, cat. 3310-10) was added for 1 hour at room temperature. Unbound conjugated enzyme was washed off and the assay was developed by adding BCIP/NBT substrate (Mabtech, cat. 3650-10). Developed ELISPOT plates were analyzed on CTL ImmunoSpot S6 Ultimate-V analyzer using Immunospot software v5.1. Responses were reported as the difference between average numbers of spots in wells stimulated with Arginase 1 and wells without added peptide.

To check for IL-4 induced Arg1 responses, PBMCs were stimulated with IL-4 (100 or 50 U/ml) and/or IL-2 (120 or 60 U/ml) for a week before being set up in the ELISPOT assay as described above.

Intracellular Staining

Intracellular staining of cell cultures was performed after PBMCs were stimulated with arginase-derived peptides for 5 hours in the presence of BD GolgiPlug™ (added after the first hour of peptide stimulation). Stimulated cells were stained with fluorescently labeled antibodies for surface markers (CD3, CD4, CD8) and thereafter permeabilized by using Fixation/Permeabilization and Permeabilization Buffer (eBioscience, cat. 00-5123-43), according to manufacturer's instructions. Permeabilized cells were then stained with fluorochrome-labeled antibodies for IFNγ and TNFα. Flow cytometry analysis was performed on a FACSCanto™ II (BD Biosciences). Antibodies used: IFNγ-APC (cat. 341117), TNFα-455 BV421 (cat. 562783), CD4-FITC (cat. 347413), CD8-PerCP (cat. 345774), CD3-APC-H7 (cat. 560275) (all from BD Biosciences), dead cells stain-FVS510 (564406, BD Biosciences) according to manufacturer's instructions.

Memory T Cell Sorting

CD4+ and CD8+ memory T cells were sorted from freshly thawed healthy donor or cancer patient PBMC samples using magnetic bead sorting kits: Memory CD4+ T Cell Isolation Kit, human (cat. 130-091-893, Miltenyi Biotec) and CD8+ Memory T Cell Isolation Kit, human (cat. 130-094-412, Miltenyi Biotec). The purity of isolated cells was assessed by staining for CD4-FITC, CD8-PerCP, CD45RO-PE (all from BD Biosciences), dead cells were stained using LIVE/DEAD™ Fixable Near-IR Dead Cell Stain Kit (Invitrogen™, ThermoFisher Scientific).

Results

Arginase 1 Peptide Length Determines the Efficiency of T Cell Stimulation

Based on the previously identified 50-amino acid long Arg1 hotspot region at positions 161-210 of Arginase 1, three different peptides that covered the major part this region were chosen, which also excluded the cysteine at position 168 of Arginase 1 (expected to improve manufacturability, solubility and stability). The three peptides were: 42-mer ArgLong (positions 169-210), 38-mer ArgLong2 (positions 169-206) and 32-mer ArgLong3 (positions 169-200).

Figure 1:
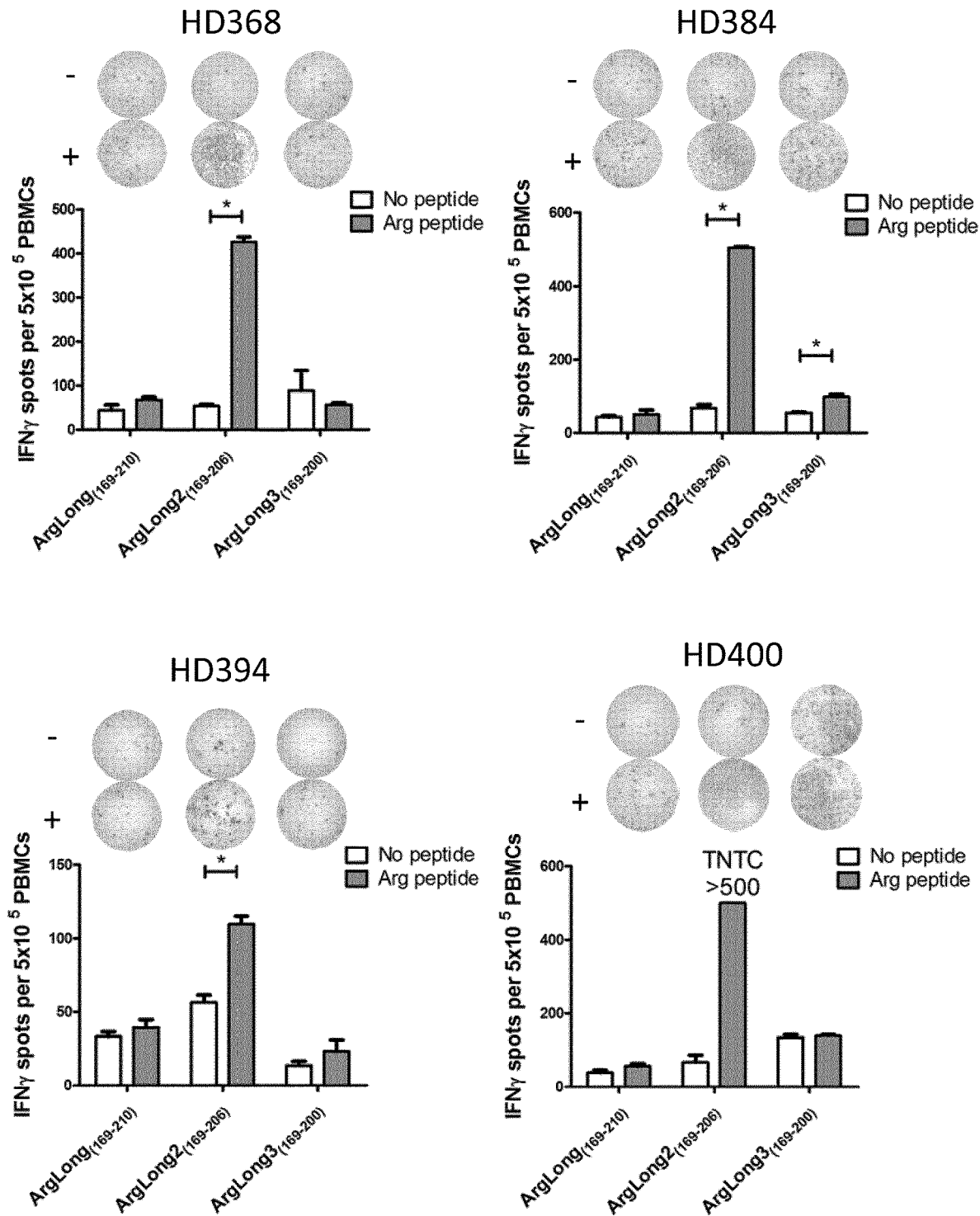
FIG. 1 shows responses against long Arg1-derived peptides

To test whether these peptides could be used to identify Arginase 1 responses, PBMCs from 6 healthy donors were screened for responses in IFNγ ELISPOT. PBMCs were stimulated with ArgLong2 peptide and low dose IL-2 for 1 week prior to ELISPOT. Despite the similarities in sequence, the ArgLong2 peptide appeared to be superior at stimulating T cell responses in IFNγ ELISPOT. As shown in FIG. 1, high responses against ArgLong2 peptide were seen in 4 out of 6 donors, while low or no responses were present against ArgLong and ArgLong3 peptides.

ArgLong2 is only 4 amino acids shorter than ArgLong and 6 amino acids longer than ArgLong3. This suggests that the peptide length and sequence may play a crucial role in ensuring optimal processing and presentation of arginase peptides. As a consequence, it may have an effect on the ability of such peptides to activate Arg1 specific T cells.

To determine whether the ArgLong2 peptide is comparable to previously described individual 20-mer peptides covering the same sequence (see WO2018065563 Examples 1, 2 and 3), PBMCs from 19 healthy donors and 16 cancer patients (8 melanoma, 6 multiple myeloma, 1 breast cancer and 1 renal cell carcinoma) were screened for responses against three 20-mer peptides and the 38-mer ArgLong2. In both cancer patients and healthy donors, ArgLong2 produced the most responses compared to all three 20-mer peptides (see FIG. 2). Strong responses against ArgLong2 were seen in 14 out of 19 healthy donors and 8 out of 16 cancer patients. Responses were also seen against 20-mer peptides, although these were fewer and lower. In summary: $Arg_{171-190}$ showed responses in 3 healthy donors and 3 cancer patients, $Arg_{181-200}$ showed responses in 4 healthy donors and 6 cancer patients, $Arg_{191-210}$ showed responses in 7 healthy donors and 3 cancer patients.

CD4+ and CD8+ Responses Against Arginase 1

Previously described T cell responses against 20-mer Arg1 peptides have shown predominantly CD4+ T cell responses in cancer patients and healthy donors (see WO2018065563 Example 2). Since the ArgLong2 peptide appeared to be more efficiently processed and subsequently recognized by T cells, the type of T cell responses to ArgLong2 was investigated by intracellular staining.

PBMCs from two healthy donors (HD384, HD400) and one breast cancer patient (BD30) that had previously shown strong responses against ArgLong2 in ELISPOT were tested by intracellular staining one week after in vitro stimulation with ArgLong2 and low dose IL-2. Remarkably, both CD4+ and CD8+ T cell responses against ArgLong2 peptide were identified in the cancer patient and healthy donors. Both CD4+ responses (left panel of FIG. 3A) and CD8+ responses (right panel of FIG. 3A) were detected in one healthy donor and in the breast cancer patient PBMCs. The other healthy donor showed only CD8+ T cell response.

Figure 3B:
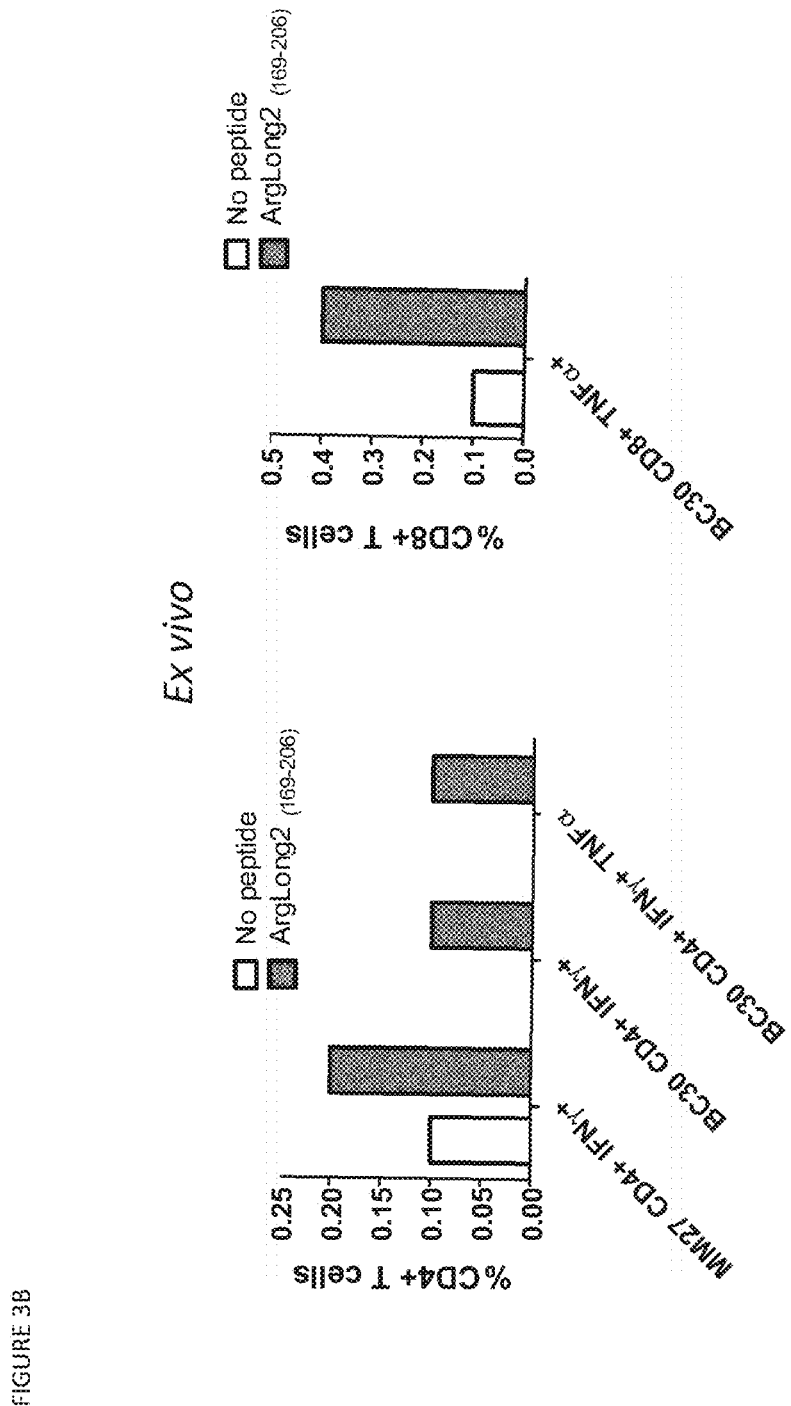

Interestingly, detectable CD4+ and CD8+ responses against ArgLong2 were also seen in intracellular staining of PBMCs without prior peptide stimulation. PBMCs from two cancer patients (one malignant melanoma (MM27) and one breast cancer (BC30)) were thawed and directly tested for responses against ArgLong2 peptide in ex vivo intracellular staining We were able to detect ex vivo CD4+ responses in PBMCs from both cancer patients (FIG. 3B, left) and ex vivo CD8+ responses in the breast cancer patient PBMCs (FIG. 3B, right).

Memory CD4+ and CD8+ Responses Against Arginase 1

Strong responses seen against ArgLong2 indicated that the frequencies of Arg1-specific T cells could be more commonly detectable in PBMCs without any prior peptide stimulation. PBMCs from 4 healthy donors and 2 cancer patients (1 breast cancer and 1 malignant melanoma) that had shown strong responses in in vitro ELISPOT were directly tested for responses to ArgLong2 peptide in ex vivo IFNγ ELISPOT. We found significant spontaneous responses in all 6 donors (See FIG. 4A).

Presence of strong spontaneous ex vivo responses against ArgLong2 peptide in PBMCs of healthy donors and cancer patient suggested that Arginase 1-specific cells are a natural part of the immune system. To test that CD4+ and CD8+ memory T cells were sorted from PBMCs of cancer patients and healthy donors that had shown a strong spontaneous immune response ex vivo. CD4+ or CD8+ memory T cells were sorted from PBMCs of 4 healthy donors and 2 cancer patients using magnetic bead sorting and set up in ex vivo IFNγ ELISPOT. The purity of memory T cell isolation was confirmed by flow cytometric analysis for CD4+ CD45RO+ and CD8+ CD45RO+ T cells and was determined to be >95%. We found CD4+ memory responses against Arg- Long2 peptide in 2 cancer patients and 3 healthy donors (see FIG. 4B). Clear CD8+ memory responses could be detected in 2 healthy donors (see FIG. 4C).

IL-4 Upregulated Arginase 1 Expression Increases T Cell Responses Against ArgLong2

Since Arg1-specific CD4+ and CD8+ memory T cells are present in both cancer patients and healthy donors, it was tested whether these T cells could be involved in immune regulation in response to upregulated Arg1 expression. Arg1 has been previously described to be upregulated in myeloid cells in response to IL-4.

First, PBMCs from a single melanoma patient that had previously been shown to have a strong spontaneous against ArgLong2 peptide response ex vivo were tested. The PBMCs were thawed and stimulated with IL-4, (50 U/ml or 100 U/ml), IL-2 (120 U/ml) or a combination of IL-4 and IL-2 (50 U/ml and 60 U/ml respectively) for one week before being tested in IFNγ ELISPOT for responses against ArgLong2. Non-stimulated cells were used as control. Strong significant responses were seen in all IL-4 stimulated groups: highest responses were seen against IL-4 stimulated groups as compared to no stimulation or stimulation with IL-2 alone, suggesting that Arg1 specific T cells are activated in response to upregulated Arg1 expression. See FIG. 5A.

Next, PBMCs from 2 cancer patients (BC30 (breast cancer), MM27 (malignant melanoma)) and 6 healthy donors that had previously shown strong spontaneous ex vivo responses against ArgLong2 were stimulated with either low dose IL-2 (120 U/ml) or IL-4 (100 U/ml) for 7 days. Non-stimulated cells were used as control. After 7 days in culture, PBMCs were tested for reactivity against ArgLong2 in IFNγ ELISPOT. 6 out of 8 cultures showed increase responses against ArgLong2 in IL-4 stimulated cultures compared to unstimulated and IL-2 stimulated controls, further confirming the possible common mechanism of Arg1-specific T cell activation in vivo. See FIG. 5B.

Discussion

The existence of Arg1 specific T cells has been previously described. Such T cells may be called "anti-Tregs" due to their role in targeting immune regulatory proteins. Anti-Treg responses against other immune regulatory proteins, such as PD-L1 and IDO have also been described. The above experiments demonstrate that Arginase 1 specific anti-Tregs are not only spontaneously present in cancer patients and healthy donors but also exist as part of memory T-cell repertoire, as responses against ArgLong2 peptide were seen in isolated CD4+ and CD8+ memory T cell populations.

In order to keep the immune balance, regulatory immune cells, e.g., Tregs, different dendritic cell subtypes, myeloid derived suppressor cells, and M2 macrophages suppress or terminate immune responses. This regulatory arm secures unresponsiveness or tolerance to self-antigens. Regulatory immune cells suppress immunity through a number of different cellular and extracellular factors. In contrast, specific anti-Tregs recognizing HLA-restricted derived epitopes which are generated from intracellular degraded antigens are able directly to eliminate regulatory immune cells. In addition, anti-Tregs can boost local immune activation by the secretion of effector cytokines.

$T_H2$-driven lung inflammation increases Arginase 1 expression in myeloid cells. Especially, IL-4, the prototypical inducer of the macrophage M2 phenotype, induced Arginase 1 upregulation. It has been shown here that Arginase 1-specific T cells are activated in response to the $T_H2$ cytokine IL-4. Hence, this suggests that Arginase 1 specific $T_H1$ cells infiltrate IL-4 increased environments and drive the immune response back into the $T_H1$ pathway, which could be an important role of Arginase 1 specific anti-Tregs in controlling the immune inhibition and promoting inflammation. However, Arginase 1-specific anti-Tregs themselves are hampered by the suppressive effects of Arginase 1 expressing regulatory immune cells. Thus, in immune regulatory networks, Arginase 1 specific anti-Tregs suppress the function of Arginase 1+ regulatory immune cells and vice versa. Hence, under normal physiological conditions equilibrium between immune activation and suppression may be necessary to maintain immune homeostasis.

The findings of memory T cells specific for Arginase 1 in healthy individuals, which are expanded in response to IL-4, is in line with previously findings regarding IDO and PD-L1 specific anti-Tregs. Circulating IDO- or PD-L1 specific anti-Tregs have been identified as present in healthy donors, although detection was not as frequent as detection in patients with cancer. Additionally, it has been found that the pro-inflammatory cytokines IL-2 and IFN-γ, which are known to induce IDO and PD-L1, expand populations of IDO- or PD-L1 specific T cells among human PBMCs without additional stimulation.

Expression of Arginase 1 in the tumor microenvironment by immune suppressive myeloid cells inhibits anti-tumor T cell responses through L-arginine depletion. In an Arginase 1 positive environment T cells cannot proliferate, and a promising therapeutic strategy is thus to reconstitute the adaptive immune responses by the activation of pro-inflammatory Arginase 1-specific T cells. Activation of Arginase 1-specific anti-Tregs by peptide vaccination offers a novel approach at targeting of a specific immune inhibitory mechanism in cancer.

Developing new immune-therapeutic approaches in cancer treatment is likely to be most efficient and versatile when common suppressive mechanisms are targeted. As shown in these experiments. Arginase 1-specific anti-Tregs exist as a natural part of the immune system and can be readily employed to tilt the balance away from immune suppression in cancer.

The peptide ArgLong2, which covers the majority of the previously described Arginase 1 hotspot region, has been shown to be particularly efficient at stimulating arginase-specific CD4+ and CD8+ T cell responses as compared to similar peptides of different lengths. ArgLong2 therefore has particularly high likelihood for success in a vaccination setting, given its potential to stimulate Arginase 1-specific anti-Tregs which may exert both effector and helper functions in the tumor microenvironment.

Example 2—Design of Additional Peptides

In order to design peptides suitable for use in vaccination experiments in mice, and which may also be functional in humans, the sequence of murine Arginase 1 (SEQ ID NO: 11) was compared to the human Arginase 1 sequence of SEQ ID NO: 10. The level of similarity is particularly high in the hotspot region of human Arginase 1 corresponding to positions 161-210 of SEQ ID NO: 1. An alignment of this region and the corresponding region in murine Arginase 1 is also shown below:

```
hArg1
                                          (SEQ ID NO: 12)
GFSWVTPCISAKDIVYIGLRDVDPGEHYILKTLGIKYFSMTEVDRLGIGK mArg1:
                                          (SEQ ID NO: 13)
GFSWVTPCISAKDIVYIGLRDVDPGEHYIIKTLGIKYFSMTEVDKLGIGK
```

Only 2 residues of the 50 differ, shown as bold and underlined. A leucine in the human sequence is substituted for the highly similar aliphatic amino acid isoleucine in the mouse, and an arginine in the human sequence is substituted for the similarly basic lysine in the mouse. Both changes are conservative. Accordingly the hotspot region is highly conserved between humans and mice. Polypeptides of the invention therefore include polypeptides which consist of a particular human sequence from the hotspot region, but in which the substitutions for the corresponding mouse sequence are made. For example, SEQ ID NO: 2 corresponds to SEQ ID NO:1 but with both the above-mentioned leucine-isoleucine and arginine-lysine substitutions. The polypeptide consists of SEQ ID NO: 2 may be referred to herein as mArgLong2. Similarly, SEQ ID NO: 4 corresponds to SEQ ID NO: 3 but with the above-mentioned leucine-isoleucine substitution. The polypeptide consisting of SEQ ID NO: 2 may be referred to herein as mArgLong3. Similarly, SEQ ID NO: 6 corresponds to SEQ ID NO: 5 but with both the above-mentioned leucine-isoleucine and arginine-lysine substitutions. The polypeptide consisting of SEQ ID NO: 6 may be referred to herein as mArgLong. The murine peptides are expected to have similar potential as vaccines to their human counterparts.

Example 3—In Vivo Experiments with Human ArgLong2 Peptide in Murine Tumor Models In order to demonstrate the therapeutic potential of vaccination using the ArgLong2 peptide, mouse models were developed. Since the corresponding ArgLong2 sequence in mice differ by only two amino acids, the human ArgLong2 sequence was employed in the subsequent experiments. A comparison of the human and mouse ArgLong2 sequences is shown below:

```
Human ArgLong2
                                        (SEQ ID NO: 1)
ISAKDIVYIGLRDVDPGEHYILKTLGIKYFSMTEVDRL Mouse ArgLong2
                                        (SEQ ID NO: 2)
ISAKDIVYIGLRDVDPGEHYIIKTLGIKYFSMTEVDKL
```

Materials and Methods

Peptide Vaccination of C57BL/6 Mice
Animals were vaccinated subcutaneously with 100 μg peptide in DMSO/H$_2$O in a 1:1 emulsion with incomplete Montanide ISA 51 VG. Montanide ISA 51 VG+DMSO/H$_2$O served as a control vaccine. For subsequent analysis of the immune response to the ArgLong2 peptide, mice were sacrificed on day 7 and spleen and draining lymph nodes (dLNs) were harvested for ELISPOT setup.
ELISPOT Analysis of Peptide-Specific Response
Murine immune cells were subjected to ELISPOT analysis. Single cell suspension was prepared from spleen or dLNs by passage through a cell strainer. After lysis of red blood cells, 0.6-0.8×10$^6$ cells/well were seeded into ELISPOT plates coated with anti-IFNγ antibody. Peptide of interest was added to designated wells and cells were incubated overnight with peptide. The next day, cells were removed, plates washed and incubated with biotinylated detection antibody. Finally, after addition of Streptavidin-ALP and substrate visible spots appear. Each spot corresponds to an individual IFNγ producing cell. Plates were analysed in an Immunospot analyser and plotted.
Tumour Vaccination of Female C57BL/6 Mice, Age 15-16/17-20 Weeks, 15 Animals Per Group
Each animal was inoculated subcutaneously into the right flank with 0.5×10$^6$ syngeneic tumour cells in 100 μl media. Both the syngeneic B16 F10 melanoma cells line and the syngeneic MC38 colon adenocarcinoma cell line were used. Vaccinations were initiated on day 0 and repeated once a week (day 7 and day 14). Peptide and control vaccinations were performed as described above.
Tumour growth was monitored and tumours were measured approximately every second day. Tumour volume was calculated at V [mm$^3$]=L×W$^2$/2 (where L is the longest diameter and W perpendicular to L). Maximum tumor size before mice were euthanized was 864 mm$^3$ (L=12 mm, W=12 mm).
Results
ArgLong2 was found to be strongly immunogenic in C57BL/6 mice, shown by high frequency of vaccine-specific T cell responses detected after just one vaccination (FIG. 6).
In the tumour studies, vaccinations with ArgLong2 significantly delay tumour growth as compared to control vaccination. The delay in tumor growth was observed in both the MC38 model for colon adenocarcinoma (FIG. 7) and the B16 model for melanoma (FIG. 8).

Example 4—ArgLong2-Specific T Cell Clones Recognize Arginase 1-Expressing THP-1 Cells Materials and Methods Generation of ArgLong2-Specific T Cell Clones
ArgLong2 clone cultures were generated from a T cell culture enriched for ArgLong2 specific cells following a standard rapid expansion protocol (REP): ArgLong2 specific cells were separated by magnetic bead sorting of TNFα producing T cells and used for limited dilution cloning in 96-well plates with ~1 cell/well. Each well contained 200 μl of REP mix (irradiated feeder cells from 3 different buffy coats, αCD3 antibody and 6000 U/ml IL-2) to promote the growth of ArgLong2-specific T cells.
Quantification of Arginase 1 mRNA in THP-1 Cells by qPCR
THP-1 cells were stimulated with 20 ng/ml IL-13 (TriChem) for 48 hrs. Cells were harvested, washed in PBS and pelleted by centrifugation at 300 g for 5 minutes. The pellets were kept on ice, resuspended in 350 μl RLT Plus-Buffer (Qiagen). RNA was purified using the RNAeasy Kit (Qiagen) according to manufacturer's instruction with final elution in 30 μl of RNA-free water. The RNA concentration was measured on the NanoDrop 2000 Spectrophotometer (Thermo Scientific). RNA was stored at −80° C.
Total RNA was reverse transcribed using the High Capacity cDNA Reverse Transcription Kit (Applied Biosystems). For each reaction, 1000 ng RNA was reverse transcribed. For RT-qPCR, the cDNA was diluted 1:5 and subjected to RT-qPCR analysis using the TaqMan Gene Expression Assay on the Roche Lightcycler 480 Instrument. RT-qPCRs were run in quadruplicates and data was analysed using the ddCT-method with normalization to expression level of the house keeping gene RPLPO and control sample. For low concentration samples that were not amplified, Ct was set to 40. No-reverse transcriptase controls (cDNA reactions setup without reverse transcriptase) served as controls of specific amplification. Arg1 human primer was purchased from Thermofisher (undisclosed sequence, product number Hs00163660_m1).
Determination of THP-1 Cell Recognition by ArgLong2-Specific T Cells
Untreated and IL-4/IL-13-treated THP-1 cells were washed and divided into two groups: HLA-DR/DQ/DP blocking antibody (clone Tü39) was added to the first group at a concentration of 10 µg/ml for 20 min at 37° C. The second group of THP-1 cells was left untreated. After 20 min HLA-II blocking THP-1 cells were washed. THP-1 cells treated with IL-4/IL-13 (with or without HLA-II block) were then mixed with ArgLong2 peptide specific T cells at effector:target ratio of 2:1 and then processed according to the standard intracellular cytokine staining protocol.

Results

In order to further evaluate the functionality of ArgLong2-specific T cells, T cell clones have been generated from a healthy donor previously identified with a strong ArgLong2 response, and their ability to specifically recognise Arginase 1-expressing targets was examined.

Th2 cytokines, such as IL-4 or IL-13 are known to upregulate ARG1 expression in myeloid cells. To test whether ArgLong2-specific T cells would specifically recognise Th2 cytokine-treated myeloid cells, the ability of ArgLong2 T cell clones to recognise HLA-matched monocytic THP-1 cell line that was pre-stimulated 48 hours with either IL-4 (100 U/ml) or IL-13 (20 U/ml) was tested.

Th2-cytokine treated THP-1 showed increased expression of Arginase 1. In this regard, FIG. 9C shows that Arginase 1 expression is induced in THP-1 cells when pre-treated with IL-13, thereby increasing presentation of Arginase 1-derived peptide epitopes on the surface of these cells.

Figure 9A:
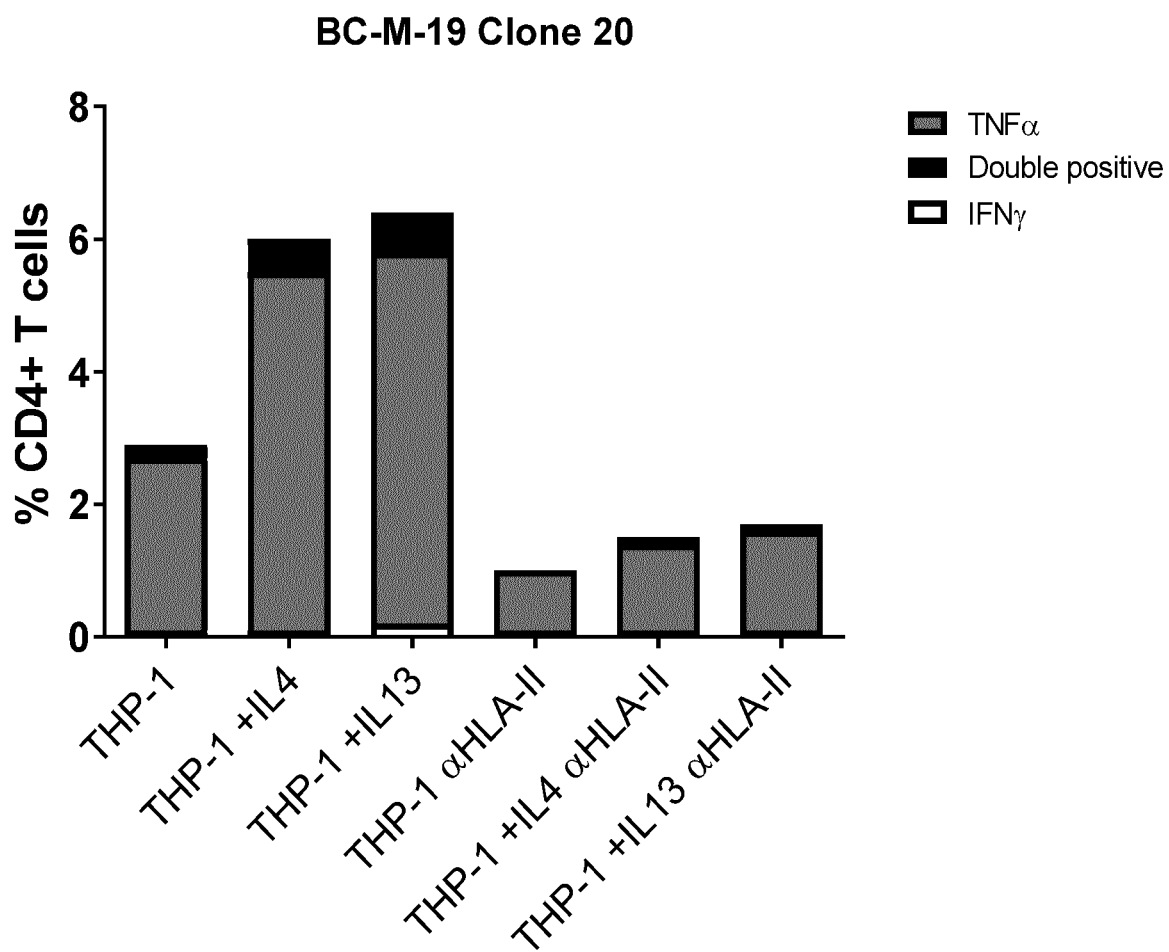
Figure 9B:
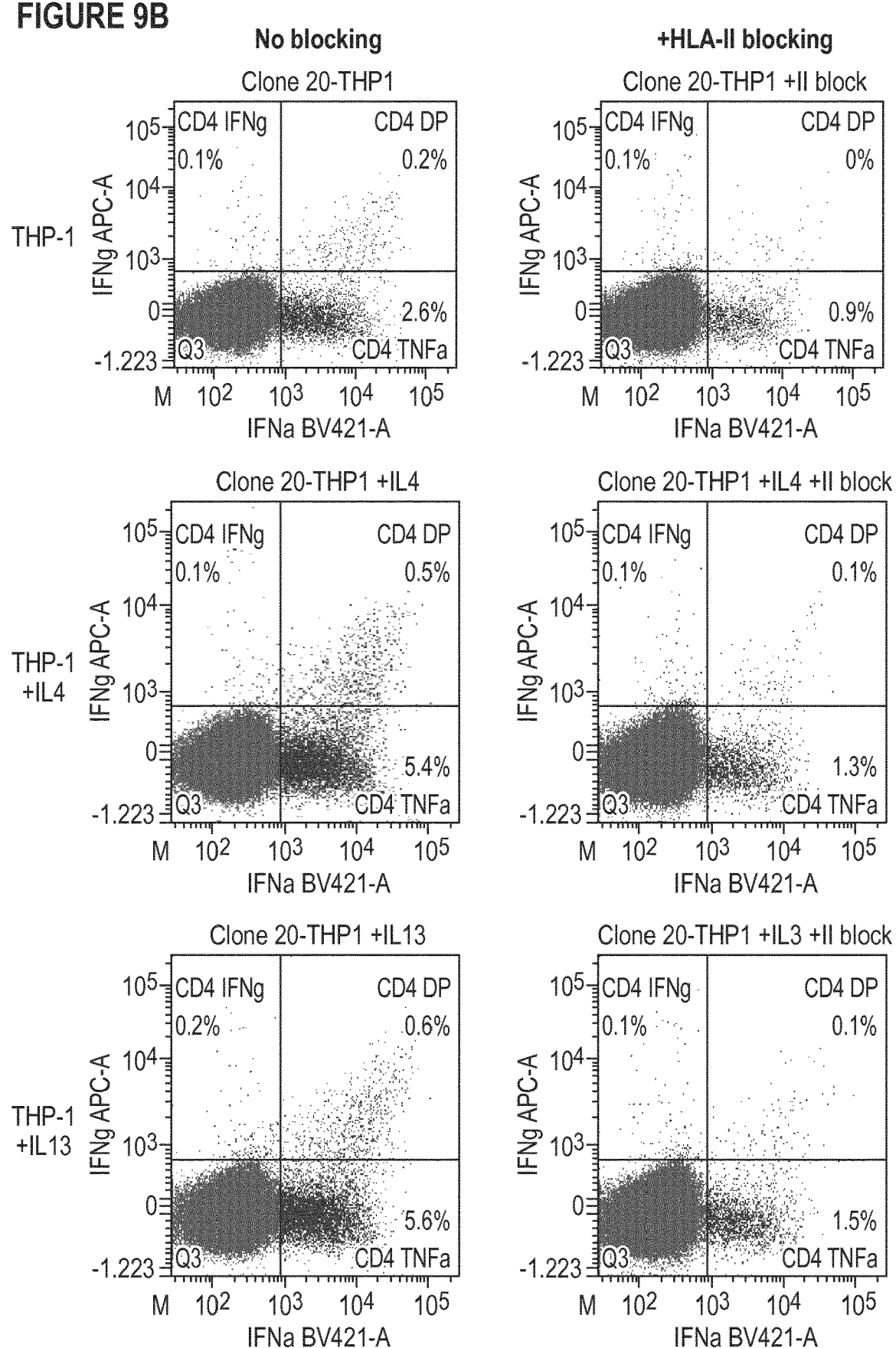
Figure 9C:
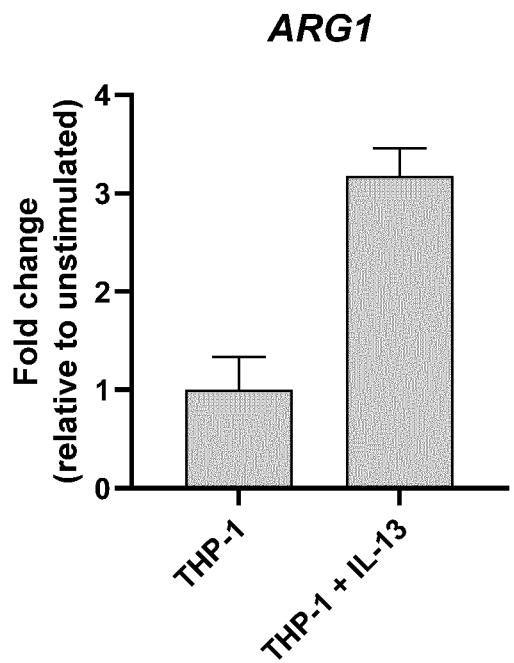

ArgLong2-specific CD4 T cell clones were shown to recognise IL-4 and IL-13 treated THP-1 cells, as indicated by the increased production of TNFα and IFNγ against these cells compared to the untreated THP-1 (FIG. 9A). Blocking of the HLA class II molecules abrogates the increased recognition of the IL-4 or IL-13 treated THP-1 cells, showing that increased recognition of the IL-4 and IL-13 treated THP-1 cells is dependent on the HLA class II presentation of ARG1 peptides. FIG. 9B illustrates representative data from FIG. 9A in dot plots format, showing the production of IFNγ and TNFα in response to IL-4 and IL-13 treated THP-1 cells without or with HLA class II blocking.

In a separate experiment, PBMCs from a healthy donor (HD22, known to have a pre-existing ex vivo response against ArgLong2) were treated with IL-4 (100 U/ml) or IL-13 (20 U/ml) for 7 days in order to increase presentation of the Arginase 1-derived peptides in the PBMC culture and thus stimulate the intrinsic ArgLong2 specific T cells present in the PBMCs. After 7 days of stimulation with IL-4 or IL-13, the PBMCs were analysed in IFNγ ELISPOT assay to check the changes in the frequency of the ArgLong2-specific T cells.

Increased ArgLong2 responses were seen in IL-4 and IL-13 treated PBMC cultures as compared to untreated control. The magnitude of the IL-13 stimulated ArgLong2 response was comparable with the responses seen after in vitro ArgLong2 peptide stimulation, suggesting a strong activation of Arginase 1-specific cells in the Th2 cytokine conditions.

SEQUENCES

| SEQ ID NO | Sequence | Name | Start pos | End pos |
|---|---|---|---|---|
| 1 | ISAKDIVYIGLRDVDPGEHYILKTLGIKYFSMTEVDRL | ArgLong2 | 169 | 206 |
| 2 | ISAKDIVYIGLRDVDPGEHYIIKTLGIKYFSMTEVDKL* | mArgLong2 | 169 | 206 |
| 3 | ISAKDIVYIGLRDVDPGEHYILKTLGIKYFSM | ArgLong3 | 169 | 200 |
| 4 | ISAKDIVYIGLRDVDPGEHYIIKTLGIKYFSM* | m7rgLong3 | 169 | 200 |
| 5 | ISAKDIVYIGLRDVDPGEHYILKTLGIKYFSMTEVDRLGIGK | ArgLong | 169 | 210 |
| 6 | ISAKDIVYIGLRDVDPGEHYIIKTLGIKYFSMTEVDKLGIGK* | mArgLong | 169 | 210 |
| 7 | AKDIVYIGLRDVDPGEHYIL | Arg1-18 | 171 | 190 |
| 8 | DVDPGEHYILKTLGIKYFSM | Arg1-19 | 181 | 200 |
| 9 | KTLGIKYFSMTEVDRLGIGK | Arg1-20 | 191 | 210 |

* indicates a sequence from murine Arginase 1 which includes at least one difference relative to the corresponding region of human Arginase 1. Residues which are non-identical with the corresponding human sequence are bold and underlined. Murine and human Arginase 1 are the same length so start and end positions are the same.

Full length human Arginase 1 (NP_000036.2) (SEQ ID NO: 10)
MSAKSRTIGI IGAPFSKGQP RGGVEEGPTV LRKAGLLEKL KEQECDVKDY GDLPFADIPN
DSPFQIVKNP RSVGKASEQL AGKVAEVKKN GRISLVLGGD HSLAIGSISG HARVHPDLGV
IWVDAHTDIN TPLTTTSGNL HGQPVSFLLK ELKGKIPDVP **GFSWVTPCIS AKDIVYIGLR
DVDPGEHYIL KTLGIKYFSM TEVDRLGIGK** VMEETLSYLL GRKKRPIHLS FDVDGLDPSF
TPATGTPVVG GLTYREGLYI TEEIYKTGLL SGLDIMEVNP SLGKTPEEVT RTVNTAVAIT
LACFGLAREG NHKPIDYLNP PK
Region identified as a hotspot for immunogenicity shown bold and underlined Full length murine Arginase 1 (NP_031508.1)(SEQ ID NO: 11)
MSSKPKSLEI IGAPFSKGQP RGGVEKGPAA LRKAGLLEKL KETEYDVRDH GDLAFVDVPN
DSSFQIVKNP RSVGKANEEL AGVVAEVQKN GRVSVVLGGD HSLAVGSISG HARVHPDLCV
IWVDAHTDIN TPLTTSSGNL HGQPVSFLLK ELKGKFPDVP **GFSWVTPCIS AKDIVYIGLR
DVDPGEHYII KTLGIKYFSM TEVDKLGIGK** VMEETFSYLL GRKKRPIHLS FDVDGLDPAF
TPATGTPVLG GLSYREGLYI TEEIYKTGLL SGLDIMEVNP TLGKTAEEVK STVNTAVALT
LACFGTQREG NHKPGTDYLK PPK

SEQUENCES

Region identified as a hotspot for immunogenicity shown bold and underlined

Hotspot in human arginase 1 - positions 161-210 of SEQ ID NO: 10
GFSWVTPCISAKDIVYIGLRDVDPGEHYILKTLGIKYFSMTEVDRLGIGK (SEQ ID NO: 12)

Hotspot in murine arginase 1 -positions 161-210 of SEQ ID NO: 11
GFSWVTPCISAKDIVYIGLRDVDPGEHYIIKTLGIKYFSMTEVDKLGIGK (SEQ ID NO: 13)
Residues which are non-identical with the corresponding human sequence are
bold and underlined.

The invention claimed is:

1. A composition comprising
an isolated immunogenic polypeptide fragment of an Arginase 1 protein, wherein the polypeptide fragment consists of ISAKDIVYIGLRDVDPGE-HYILKTLGIKYFSMTEVDRL (SEQ ID NO: 1); and
a therapeutically effective amount of an adjuvant.

2. The composition of claim 1, further comprising at least one pharmaceutically acceptable diluent, carrier, or preservative.

3. The composition of claim 1 wherein the adjuvant is selected from the group consisting of bacterial DNA based adjuvants, oil/surfactant-based adjuvants, viral double stranded RNA (dsRNA) based adjuvants, imidazoquinolines, and a Montanide ISA adjuvant.

4. A method of treating or preventing a cancer characterized by increased Arginase activity in a subject comprising administering to the subject:

(a) an isolated immunogenic polypeptide fragment of Arginase 1, wherein the polypeptide fragment consists of ISAKDIVYIGLRDVDPGE-HYILKTLGIKYFSMTEVDRL (SEQ ID NO: 1);
or
(b) a composition comprising an adjuvant and the polypeptide of (a).

5. The method of claim 4, wherein the cancer is breast cancer, lung cancer, colon cancer, prostate cancer, melanoma, or a leukaemia.

6. The method of claim 4, further comprising the simultaneous or sequential administration of an additional cancer therapy.

7. The method of claim 6, wherein the additional cancer therapy is an antibody.

8. The method of claim 5, wherein the leukaemia is acute myeloid leukemia (AML).

* * * * *